United States Patent
Biglieri et al.

(10) Patent No.: US 8,126,245 B2
(45) Date of Patent: Feb. 28, 2012

(54) APPARATUS FOR MAGNETIC RESONANCE IMAGING OF PATIENTS WITH LIMBS, PARTICULARLY LOWER LIMBS, UNDER NATURAL STRESS

(75) Inventors: Eugenio Biglieri, Masio (IT); Luigi Satragno, Genoa (IT)

(73) Assignee: Esaote, S.p.A., Casale Monferrato (IT)

( * ) Notice: Subject to any disclaimer, the term of this patent is extended or adjusted under 35 U.S.C. 154(b) by 756 days.

(21) Appl. No.: 12/303,247

(22) PCT Filed: Jun. 1, 2007

(86) PCT No.: PCT/EP2007/055424
§ 371 (c)(1),
(2), (4) Date: Dec. 2, 2008

(87) PCT Pub. No.: WO2007/141221
PCT Pub. Date: Dec. 13, 2007

(65) Prior Publication Data
US 2009/0310841 A1    Dec. 17, 2009

(30) Foreign Application Priority Data
Jun. 6, 2006  (IT) .............................. SV2006A0015

(51) Int. Cl.
*G06K 9/20* (2006.01)
(52) U.S. Cl. ....................................................... 382/131
(58) Field of Classification Search .................. 382/138, 382/131, 170–172
See application file for complete search history.

(56) References Cited

U.S. PATENT DOCUMENTS

| | | | |
|---|---|---|---|
| 5,008,624 A | 4/1991 | Yoshida | |
| 5,565,834 A | 10/1996 | Hanley et al. | |
| 6,801,031 B1 | 10/2004 | Stephan | |
| 2005/0248347 A1 | 11/2005 | Damadian | |

FOREIGN PATENT DOCUMENTS

| | | |
|---|---|---|
| EP | 0 637 755 A1 | 2/1995 |
| EP | 0 654 675 B1 | 5/1995 |
| EP | 0 875 768 B1 | 11/1998 |
| EP | 0 921 408 B1 | 6/1999 |
| EP | 0 927 889 B1 | 7/1999 |
| EP | 0 984 292 | 3/2000 |
| EP | 0 984 293 A1 | 3/2000 |
| EP | 1 462 816 A2 | 9/2004 |

(Continued)

OTHER PUBLICATIONS

Form PCT/ISA/210 (International Search Report) dated Oct. 5, 2007.
Form PCT/ISA/237 (Written Opinion of the International Searching Authority) dated Oct. 5, 2007.

*Primary Examiner* — Marcos D. Pizarro
(74) *Attorney, Agent, or Firm* — Buchanan Ingersoll & Rooney PC

(57) ABSTRACT

An apparatus for magnetic resonance imaging of patients with limbs, particularly lower limbs, under natural stress, which apparatus includes a magnet structure having an open or closed annular shape, and a predetermined axial extension, which structure delimits a cavity for receiving at least a part of the patient body, with at least two or three open sides, the open sides providing access to the cavity. The open or closed annular magnet structure being disposed with the axis of the open or closed annular shape oriented with at least one vertical directional component and devices being provided for vertical translation of the magnet structure or the patient relative to the magnet structure.

58 Claims, 23 Drawing Sheets

FOREIGN PATENT DOCUMENTS

| | | | |
|---|---|---|---|
| EP | 1462816 A2 * | 9/2004 | |
| EP | 921408 B1 * | 8/2006 | |
| EP | 875768 B1 * | 11/2006 | |
| JP | 2-036842 A | 2/1990 | |
| JP | 2003-334175 A | 11/2003 | |
| JP | 2003-334176 A | 11/2003 | |
| WO | WO 00/33722 A2 | 6/2000 | |
| WO | WO 03/052441 A1 | 6/2003 | |

* cited by examiner

APPARATUS FOR MAGNETIC RESONANCE IMAGING OF PATIENTS WITH LIMBS, PARTICULARLY LOWER LIMBS, UNDER NATURAL STRESS

TECHNICAL FIELD

The invention relates to an apparatus for magnetic resonance imaging of patients with limbs, particularly lower limbs, under natural stress, which apparatus comprises a magnet structure having an open or closed annular shape, and a predetermined axial extension, which structure delimits a cavity for receiving at least a part of the patient body, with at least two or three open sides, said open sides providing access to the cavity.

BACKGROUND OF THE INVENTION

Magnetic resonance imaging apparatus of the above type are already known in the art. In prior art apparatus, the patient is placed on a patient table or a support structure, to which he/she/it is secured and by which he/she/it is displaced relative to the chamber or the cavity.

It is known that the magnet structure comprises means for generating a static magnetic field in the chamber or the cavity. It is also known that the static magnetic field must have a high homogeneity in the area coincident with that of which valid, i.e. useful images are desired. Therefore, since the openings of the magnet structure naturally generate distortions of the static field, such field cannot have the necessary or required characteristics for obtaining useful or valid images throughout the volume of the chamber, its validity being restricted to a smaller volume portion of the complete volume of the chamber. The said portion of the volume of the chamber which is permeated by the static field having the desired qualities for imaging is generally known as imaging volume, and is delimited by an ideal spherical surface.

Therefore, the imaging volume is a portion of the entire cavity or chamber volume, delimited by the surface of an ideal sphere, within which spherical surface the static field has the homogeneity required for magnetic resonance imaging.

In addition to the simple spherical shape, ellipsoidal surfaces or combinations of ellipsoidal and spherical surfaces having variously inclined axes may be used as ideal delimiting surfaces for the volume permeated by the magnetic field having the homogeneity required for magnetic resonance imaging.

Two opposite approaches are used in prior art apparatus. On the one hand, there is the tendency to make very large magnet structures, having a large cavity, wherefore the imaging volume is also large and may envelope and extend over several anatomic regions of a human or animal patient body. On the other hand, a slice-like imaging volume is provided, whereby one slice at a time is imaged, like in tomography.

In the former case, the magnet structure is very large and designed to accommodate the whole patient therein. This solution is suitable, although expensive, for human patients or small animals, but causes problems, when used in veterinary applications, if the patient to be treated has a relatively large size, such as a horse or the like.

Furthermore, particular means, as well as a certain effort are needed for positioning an animal patient on a support structure in an unnatural position, and in some cases the animal must be even anesthetized or narcotized to be secured to the structure. This requires the use of drugs and a long and difficult imaging procedure, as well as special bulky means for positioning, displacing and safely holding the patient to the support structure, particularly when the patient is an animal.

The other approach, that uses very small magnet structures to generate an image as a sum of images of slices of an anatomic region, requires long scan times, wherefore interventions, arrangements and devices are needed to hold at least the patient body part to be imaged in a stable and fixed position. If the patient is an animal, possibly of relatively large size, then the devices required to hold at least the relevant anatomic region of the animal in position for a long time are definitely bulky, hence the magnet structure shall be accordingly adapted to accommodate at least a portion of the patient support device, wherefore the magnet structure shall also have a relatively large size, which neutralizes the advantage provided by the small size of the magnet structure used for multi-slice imaging.

SUMMARY OF THE INVENTION

The invention addresses the problem of providing a magnetic resonance imaging apparatus, particularly for imaging human or animal patients, whereby the patient or the anatomic region thereof to be imaged may be brought to the proper position within the imaging volume without substantially requiring the patient to be placed on supports that force him/her/it into unnatural postures.

The invention solves the above problem by providing an apparatus for magnetic resonance imaging of patients with limbs, particularly lower limbs under natural stress, which apparatus comprises a magnet structure having an open or closed annular cross section, and a predetermined extension along the axis of the said open or closed annular cross section, which structure delimits a chamber or a cavity for receiving at least a part of the patient body, with at least two or three open sides, said open sides providing access to the chamber or the cavity, wherein the magnet structure having an open or closed annular cross section is disposed with the axis of the open or closed annular cross section oriented with at least one component in a vertical direction, whereas means are provided for vertically displacing said magnet structure and/or the patient relative to one another.

In other words the invention relates to an MRI apparatus which is destined to carry out imaging of lower and/or upper limbs of a patient in different conditions of natural stress of the said upper and/or lower limbs and which MRI apparatus comprises a scanner, the scanner comprising:

A chamber for housing at least part of an upper or of a lower limb to be examined, which chamber being opened at two opposite ends, which ends forms openings for the limb to enter and/or exit the chamber;

The chamber being delimited along a lateral wall having an annular cross section which can have an extension of 360° or less, particularly between 360° and 270°;

The lateral wall having a predetermined extension in the direction of a longitudinal axis of the chamber which passes the two opposite opened ends The scanner being provided with means for generating a static magnetic field inside the said chamber;

The scanner being provided with means for transmitting signals for exciting magnetic resonance signals to be generated by the limb or part of the limb introduced inside the said chamber;

The scanner being provided further with means for receiving or picking up the magnetic resonance signals emitted by the limb or part of the limb housed inside the said chamber.

According to an embodiment of the present invention, the scanner is supported in a position in which the longitudinal axis of the chamber has at least one component oriented in a vertical direction and/or one of the open ends of the scanner is oriented upwards, while means are provided for supporting the scanner and/or at least the limb of the patient in a vertically displaceable way relatively to one another.

Thanks to these arrangements, the human or animal patient may enter the cavity, or an anatomic part thereof may be received in said cavity, with the human or animal patient assuming a natural posture, and particularly a natural standing posture.

Particularly, besides being vertically translated, the scanner or the magnetic structure may be also supported in such a manner as to oscillate about a horizontal axis, so that the vertical component of the axis of the chamber or cavity may be adjusted.

Still according to one or more of the preceding claims the scanner or the magnetic structure is supported in such a way as to be able to rotate around the longitudinal axis of the chamber or of the cavity.

When the scanner or the magnetic structure have an annular cross section either closed or open, the said scanner or the said magnetic structure are rotatable around the axis of the said closed or opened annular cross section.

In one embodiment, the end position is the one in which the axis of the open or closed annular cross section of the magnetic structure or the longitudinal axis of the chamber of the scanner is vertical, and its displacement follows an upward and downward vertical direction.

In a variant thereof, the magnetic structure or the chamber of the scanner is oriented with its axis tilted 45° with respect to the vertical and/or horizontal directions.

The magnetic structure or the scanner is provided at least on one of the lateral walls of the magnetic structure with a reduced thickness, which is smaller than the natural distance between the lower limbs of the animal or human patient.

Particularly this is achieved by providing at the outside of the magnetic structure or of the body of the scanner with an indentation which has an extension parallel to the longitudinal extension of the chamber and which bottom wall has a distance from the opposing wall delimiting the chamber which is smaller than the natural distance between the lower limbs of the animal or human patient.

In this case, the thickness of this wall may be smaller than it would typically be to fit the average distance between the lower limbs of the smallest patient typically designed to be treated by the magnetic resonance imaging apparatus.

According to a preferred embodiment the magnetic structure or the scanner has one of the said indentation on opposite sides of the chamber, particularly on diametrically opposite sides of the chamber when the scanner body and the chamber has an annular cross section.

When the scanner body and the chamber have an annular cross section which is open on one side, the chamber has an opening along the lateral wall having a longitudinal extension from one to the other of the said opened opposite ends and the two indentations are provided on opposite sides of a central longitudinal plane of the chamber and of the lateral opening.

According to an improvement of the invention the above described MRI apparatus is provided in combination with means for blocking an upper or lower limb to assume a predetermined posture, particularly to assume a certain bending of the articulation of the said limb, namely the knee or the elbow, which means also are able to block the said limb in the said certain posture.

An embodiment of such a device comprises at least one rigid shell or surface to be secured against a predetermined part of the limb and which is anatomically shaped in a corresponding way to the shape of part of the limb to which it has to be secured in the predetermined posture of the said limb, while the said shell is secured by means for tightening it to the limb, such as one or more belts or tightening straps surrounding the limb.

Two or more rigid shells may be provided in combination which are shaped according to the anatomy of different parts of the limb and which can be secured together to the limb by the said tightening means.

One further embodiment of the said device comprises at least two shells which are shaped correspondingly to two diametrically opposed sides of the limb while tightening means are provided for tightening the two shells one against the other thus blocking the limb between them in the posture defined by the shape of the said shells.

The limb can be a leg or an arm. According to one embodiment the said device is a device for blocking a leg in a certain condition of bending of the knee, particularly corresponding to a slight flexion of the knee of about 5 to 20 degrees. This posture of the leg corresponds to a normal posture of bending the knee under natural gravitational stress.

According to a further improvement the said rigid shell or shells comprises two or more rigid segments which are connected one with the other thanks to hinge means allowing the said segments to be inclined one with respect to the other.

According to still another improvement the said device for blocking the limb in a predetermined position is combined with the means for receiving or picking up the magnetic resonance signals, such as an MRI receiving coils.

In this case the rigid shell and/or the tightening means forms the enclosure for housing the said receiving means, for example the said receiving coils.

Still according to another improvement, which is provided in combination with the above mentioned means for blocking the limb in a predetermined posture, the chamber has an elongated cross section along the plane which is transversal to the longitudinal axis of the said chamber, particularly an elliptic, oval or rectangular cross section which can be closed or open. Thanks to this at leas one dimension or radius of the chamber can be limited to a radius which is slightly greater than the maximum radius of a circle enclosing the biggest limb cross section, while in the perpendicular direction the chamber has a radius which is notatably greater than the said maximum radius of a circle enclosing the biggest limb cross section, thus allowing the said inclined or bent posture of the knee or of an elbow.

As mentioned above, the scanner or the magnetic structure may have an open or closed annular cross section. The term open annular cross section is meant to indicate C- or U-shaped magnet structures.

In this case, i.e. when using open U- or C-shaped magnetic structures or scanners with one of the open sides oriented along at least one of the directional components of the static field Bo, the magnet structure is disposed with the axis of the annular cross section, i.e. the axis of the two opposite open end sides, oriented vertically, and with the open side parallel to one of the components of the magnetic field and to said axis. In this case, the magnetic structure is oriented with said open side, which is parallel to the axis of the annular cross section, perpendicular to center-to-center distance between two adjacent lower limbs or to the plane subtended by two adjacent lower limbs. Therefore, when one of the two adjacent limbs is imaged, the other limb is in a comfortable natural position at the vertical open side of the magnet structure.

To increase comfort while reducing the size of the magnet structure, the C-shaped magnetic structure or scanner is formed with a flared or step-like enlarged configuration at said vertical open side. This configuration may be obtained using one or more of the combinations disclosed in EP 921 408.

Alternatively or in addition, according to the invention at least one of the two walls that form the two opposite branches of the said magnetic structure having an U-shaped cross section has a thickness that is smaller than the lateral distance between the two limbs and the magnet is disposed with the axis of the open side oriented perpendicular or transverse to the lateral alignment axis of two adjacent lower limbs.

According to a further feature, the magnetic structure or the scanner may be arranged to be extensible in at least one direction which is transversal to the axis of the annular cross section.

When the magnetic structure has an open annular shape or cross section, this may be extensible parallel to the open side of the said open annular shape or cross section, which is oriented perpendicular to the open end sides of the said annular cross section or shape.

In this case, means may be provided for adjusting at least the static field strength. If the magnetic structure or chamber uses permanent magnets as magnetic field generating means, additional magnetized elements may be provided, whose magnetization has predetermined magnitude and direction which are determined according to the predetermined dimensional adjustments of the magnetic structure, which elements can be mounted in predetermined positions in the magnetic structure by means of removable attachment means to the magnetic structure.

Here, these additional magnetized elements may be provided in the form of multiple arrays of elements, each composed of a given number of elements having a predetermined magnetization, in terms of both magnitude and direction of the magnetization vector, and each of which arrays are provided with means for removable attachment to predetermined parts of the magnetic structure, while each of the said arrays is designed for integration of a magnetic structure having a minimum base configuration to fit a predetermined size of such magnetic structure and particularly a predetermined length in a direction parallel to the open side of the open annular structure.

Referring to a variant in which the field generating means are resistive or superconducting magnets, according to the invention the strength of the magnetic field generated thereby is adapted to the selected size of the magnetic structure, by adjusting the magnetic field generating current supplied to the resistive or superconducting magnets or by providing additional resistive or superconducting magnets, which are further turned on or off depending on the selected magnet structure size.

One solution may further provide a combination of permanent magnets and resistive or superconducting magnets in the magnet structure. In this case, the smallest base magnet structure is the one in which the magnetic field is only or substantially generated by permanent magnets, whereas as its size increases, an increasing number of resistive or superconducting magnets are turned on, or the field generating currents supplied to such resistive or superconducting magnets are adjusted.

The above is described in greater detail, with reference to field generating means of the resistive or superconducting type as disclosed in patent application EP 875 768, by the owner hereof.

Referring to the embodiment in which the magnetic structure or the scanner having an annular cross section is oriented with the axis of the annular cross section in a position tilted 45° with respect to the vertical or horizontal direction, the invention provides further particular features.

Here, with a magnetic structure or with a scanner and an opening having a constant size in the plane perpendicular to the axis of the annular cross section, and considering the axial dimension of the chamber, i.e. the depth or thickness of the torus, if both examination kinds of natural standing patient positioning and natural horizontal, i.e. patient lying positioning are desired, a passage opening or a chamber opened end of a size similar to that of a magnetic structure in the horizontal and vertical position respectively may be only obtained if the opening radius or extension perpendicular to the axis of annular cross section of the magnetic structure or of the scanner is definitely larger when the magnetic structure or the scanner is positioned with the axis of its annular cross section tilted 45° than when it has an horizontal or vertical orientation.

However, according to the invention, the useful passage opening size or the span is considerably increased in both vertical and horizontal directions when the inner surfaces of the torus forming the magnetic structure or of the toroidal scanner, which surfaces delimit and form the shell wall that defines the patient limb receiving cavity or chamber are flared or outwardly inclined at an angle of 45° and are mutually connected by an intersection edge at an intermediate plane of the magnetic structure or of the scanner, perpendicular to the axis of such annular cross section. Preferably, this plane is the median plane perpendicular to the axis of the annular cross section of the magnetic structure or of the scanner.

In this case, the magnetic field generating means may have a stepped cross section, as taken in a plane parallel to the axis of the annular shape.

When the magnetic field generating means are permanent magnets, the magnetic field generating means may consist of an array of elements, either magnetized or not, such as blocks, which may be connected together and to a bearing member of the magnetic structure so that the envelope surface of the array of blocks on the cavity side is a stepped surface approximating the inclined surface of the ideal shape of the inner shell surfaces of the annular magnetic structure, and particularly a 45° inclined surface when the annular magnet structure has a 45° tilt.

Alternatively, there may be provided magnetic field generating means of the permanent magnet type, consisting of an array of elements, either magnetized or not, such as blocks, to be connected together and to a bearing member of the magnetic structure, which have rectangular and triangular sections, so that the envelope surface of the array of blocks on the cavity side is an inclined surface that coincides with the inclined surface of the ideal shape of the inner shell surfaces of the annular magnet structure, and particularly a 45° inclined surface when the annular magnet structure has a 45° tilt.

In both the above cases, the teaching of patent application EP 921 408 may apply to the present magnetic structure. First, each step may be formed of such a combination of magnetized elements that the magnetic field generated in the widened portion of the step has an higher magnetic potential than the next narrower portion of the step, i.e. closer to the median plane perpendicular to the axis of the annular structure.

Also, as more specifically taught by EP 921 408, a neodymium insert may be provided for each step, whose magnetization is oriented parallel to the axis of the annular structure from the outer end side perpendicular to the axis of the annular structure to the median plane, still perpendicular to the axis of the annular structure.

In addition or alternatively to the above arrangements, still referring to an annular magnetic structure or scanner disposed with the axis of the annular cross section at 45° with respect to a vertical or horizontal plane, the imaging volume may have a non spherical shape, more precisely an elliptical shape with the axis of the ellipse parallel to the direction in which the limb is introduced in the cavity. In this case, the imaging volume has an elongated shape in the insertion direction of the limb in the chamber of the magnetic structure or of the scanner.

Also, a spherical imaging volume may be always provided in the first instance, to be later subjected to a shimming process, i.e. a configuration and correction of the magnetic field within an elliptical volume, the spherical imaging volume being inscribed in such elliptical volume. By this arrangement, the spherical imaging volume may be considerably increased with respect to the cavity size at least in the insertion direction.

The provision of shimming means, i.e. magnetized or magnetizable shimming elements in the form of resistive or superconducting magnets, allows to adjust the orientation of the longer axis of the ellipsoid within which the magnetic field is optimized, depending on the direction of insertion of the body to be imaged, e.g. a horizontal or vertical direction, whereby the diameter of the imaging volume is always maximized according to the direction of insertion of the body to be imaged.

Shimming, i.e. magnetic field optimization in ellipsoidal volumes, is described in greater detail in In a very simple embodiment, the magnetic structure or the scanner having an open or closed annular cross section has an open or closed inner shell surface with a square or rectangular shape, which delimits a rectangular cavity or chamber which is open at two opposite end sides perpendicular to the axis of the annular cross section. If the annular structure has an open shape, one of the four inner shell walls is at least partly or wholly missing, the annular rectangular or square plan shape being open at least at a portion of one of the walls parallel to the axis of the annular shape.

In both cases, the annular or toroidal magnetic structure or scanner has at least two diametrically opposite walls with respect to the axis of the annular cross section or of the torus, which diametrically opposite walls support or form magnetic field generating means at least over part of their thickness, i.e. of their radial dimension with respect to the axis of the annular cross section or of the torus.

As described above, these means may be combinations of permanently magnetized material and metal having a predetermined magnetic permeability or resistive or superconducting magnets formed of combinations of coils and cores or combinations of permanently magnetized material and resistive or superconducting magnets.

In this case, the invention proposes two alternatives. In a former solution, the walls of the magnetic structure parallel to the axis of the annular cross section, which connect the diametrically opposite walls that support or form the magnetic field generating means are relatively thin, i.e. their thickness is smaller than the minimum distance between the lower limbs of the smallest patient body that can be treated by the apparatus.

When the magnet structure is or may be tilted at an angle of 45°, then such tilt may occur along an axis parallel to one of the two pairs of diametrically opposite walls, i.e. the connection walls between the walls that form or support the magnetic field generating means or the walls that form or support the magnetic field generating means respectively.

Further features or improvements of the invention will form the subject of the dependent claims.

BRIEF DESCRIPTION OF THE DRAWINGS

The features of the invention and the advantages derived there from will be understood more clearly form the following description of some embodiments illustrated without restriction in the accompanying drawings, in which:

FIG. 7 is shown by a, dashed line.

DETAILED DESCRIPTION OF THE PREFERRED EMBODIMENTS

Referring to the Figures, an MRI scanner or a magnetic structure for a magnetic resonance imaging apparatus is schematically shown. As it is known to those skilled in the art, in addition to the yoke and to the magnetic field generating means, which form the greatest part of the magnetic structure, the apparatus also includes gradient coils, coils for transmitting RF nuclear spin excitation pulses, receiving coils, temperature control means, electromagnetic shields, as well as other devices, which will not be illustrated or described in detail herein, as their provision is part of the ordinary skills in the art. This also applies to the electronic means required to control the apparatus and to generate images from the received RF signals.

Furthermore, this description is limited to embodiments of the scanner or of the magnetic structure in which the magnetic field generating means are elements of permanently magnetized material. This limitation shall not be intended to extend to the teaching of the invention. Thus, the features described herein also apply, directly or using characteristics known to those skilled in the art, to resistive or superconducting static field generating means or to combinations of all of these magnetic field generating means.

Figure 1:
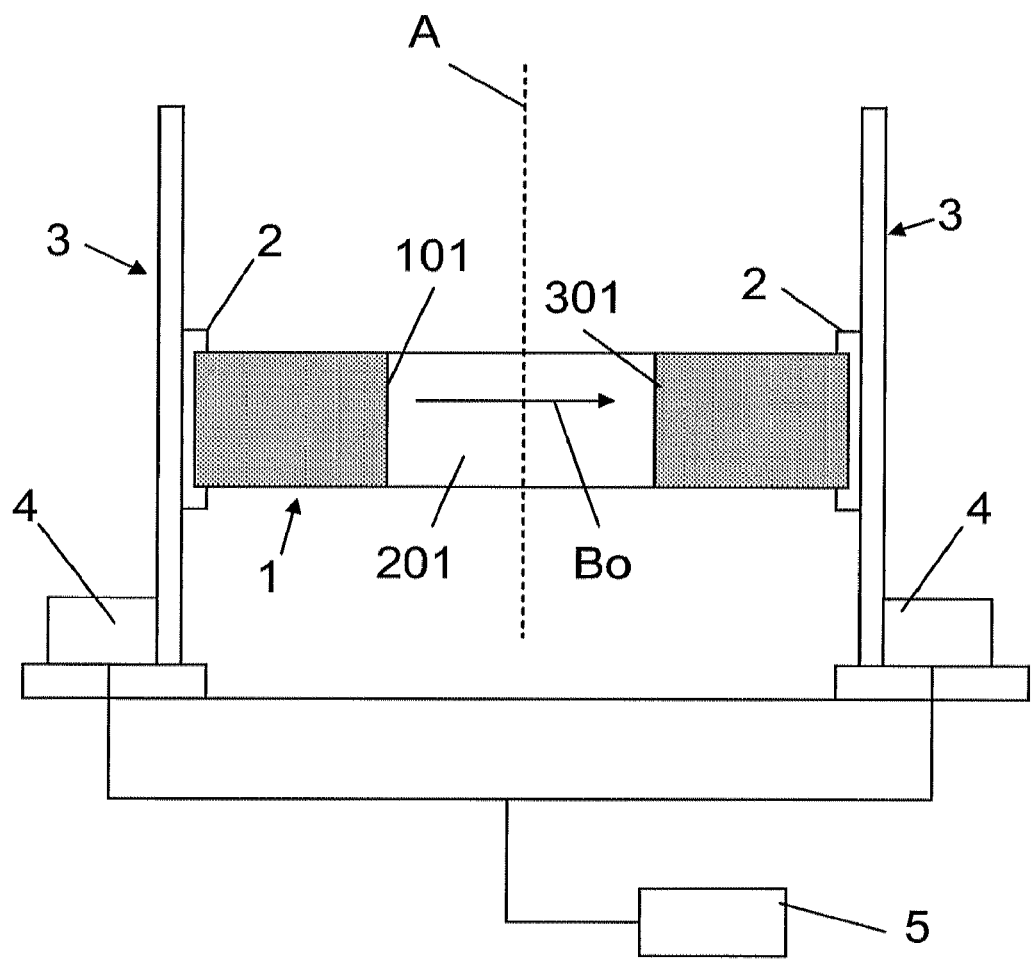
FIG. 1 is a diagrammatic side view of a magnetic resonance imaging apparatus in which the annular magnet structure is disposed with the axis of the annular shape oriented vertically.
Figure 2:
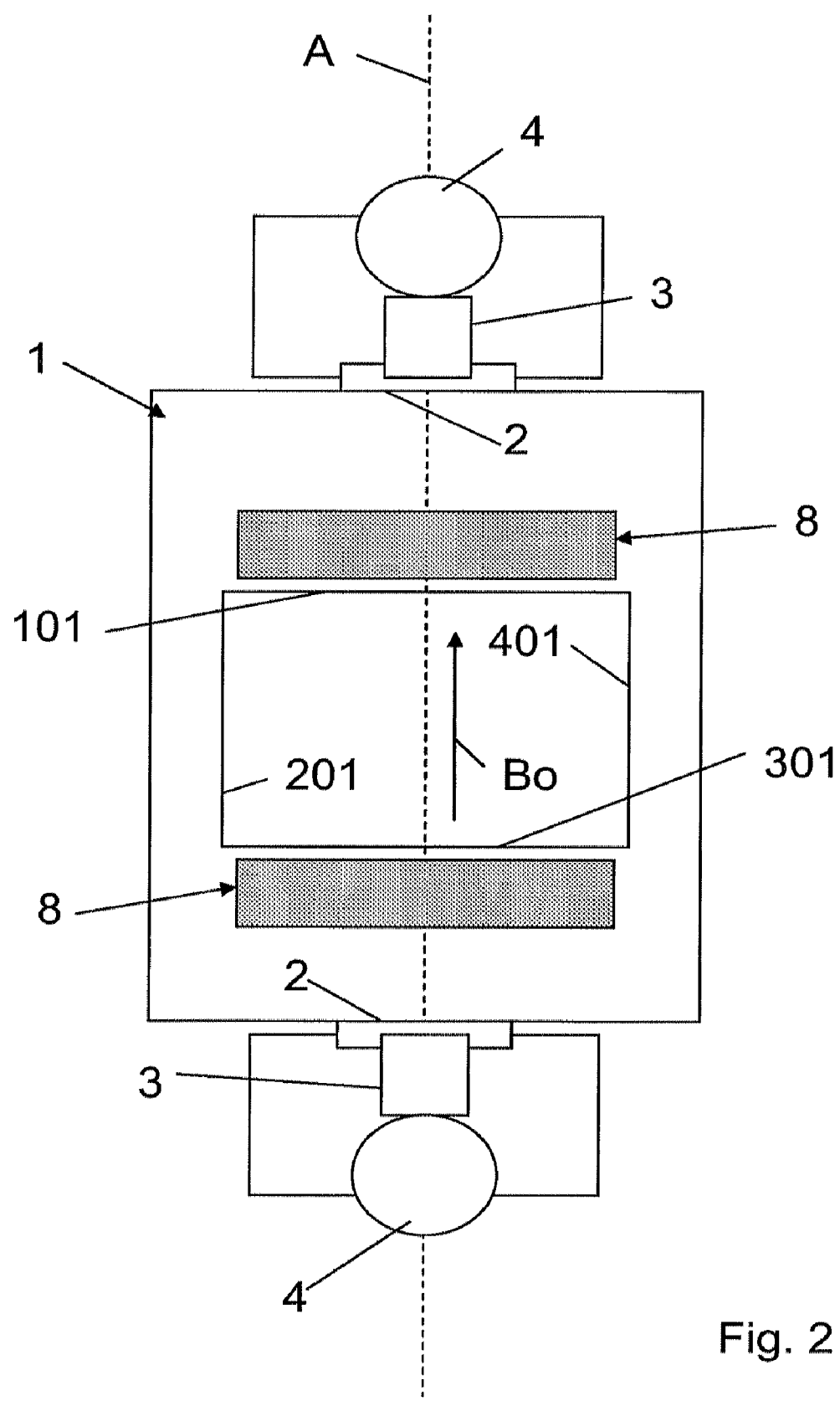
FIG. 2 is a plan view of the apparatus as shown in FIG. 1.

Referring to FIGS. 1 and 2, these Figures show a first embodiment of a magnetic resonance imaging apparatus comprising a scanner or a magnetic structure 1 having a closed annular cross section or shape. This kind of annular or toroidal magnetic structure or scanner of this example has a rectangular or square plan shape, and is composed of four walls. The axis of the annular cross section is oriented vertically. The walls of the annular or toroidal structure 1 delimit a cavity or chamber that is open at the two sides oriented perpendicular to the axis of the annular cross section of the magnetic structure or scanner 1 and the cavity or chamber is delimited by the four inner shell walls 101, 201, 301, 401 of the magnetic structure or scanner body 1. Two opposite shell walls 101, 301 form, over at least part of their thickness, i.e. their radial dimension with reference to the axis of the annular cross section of the magnetic structure 1, which axis is indicated by a dashed line A in FIGS. 1 and 4, means for generating a static magnetic field Bo, or support such means and which means are designed to permeate the chamber or the cavity delimited by the magnetic structure and the inner shell walls of the annular shape 101, 201, 301, 401.

The magnetic structure may be formed by an annular yoke, which is composed, for example, of metal plates that form an external annular or toroidal element, with its inner faces being covered by further wall elements, e.g. layers of a material adapted to generate a magnetic field, such as a permanently magnetized material or resistive or superconducting coils for generating a magnetic field with respective cores or metal elements that form pole pieces to be associated to the magnetized material or the coils.

The means for generating the static magnetic field, designated by Bo, are schematically indicated in FIG. 2 and designated by numeral 6.

The annular magnetic structure 1 is supported at least at two opposite walls by two sliding blocks 2 each being slidably fitted in a corresponding vertical guide 3. The sliding blocks are connected to displacement means, which may be motor-driven. These may be provided in several different forms, i.e. as mechanical, electromechanical or hydraulic or pneumatic means.

In an embodiment in which mechanical means are provided for driving the displacement of the sliding block, motors 4 are provided for rotatably driving, for instance, a screw on which a nut screw or a threaded bush is non rotatably engaged and slides in the longitudinal direction of the guide 3, thereby carrying a sliding block.

Otherwise, the sliding blocks may be mounted on a rod of a cylinder actuator. The two motors 4 are controlled by a common drive control unit 5 so that the two sliding blocks 2 perform identical translational motions along the two guides 3, and the magnet structure 1 is displaced parallel to itself.

Referring to FIG. 2, the illustrated magnetic structure has field generating means, generally designated by numeral 8, which are formed and/or supported by the walls that form the inner shell surfaces 101, 301. This example shall be intended without limitation, as one of the possible embodiments of field generating means, the base configurations whereof are known to the skilled person and can be freely selected.

Figure 3:
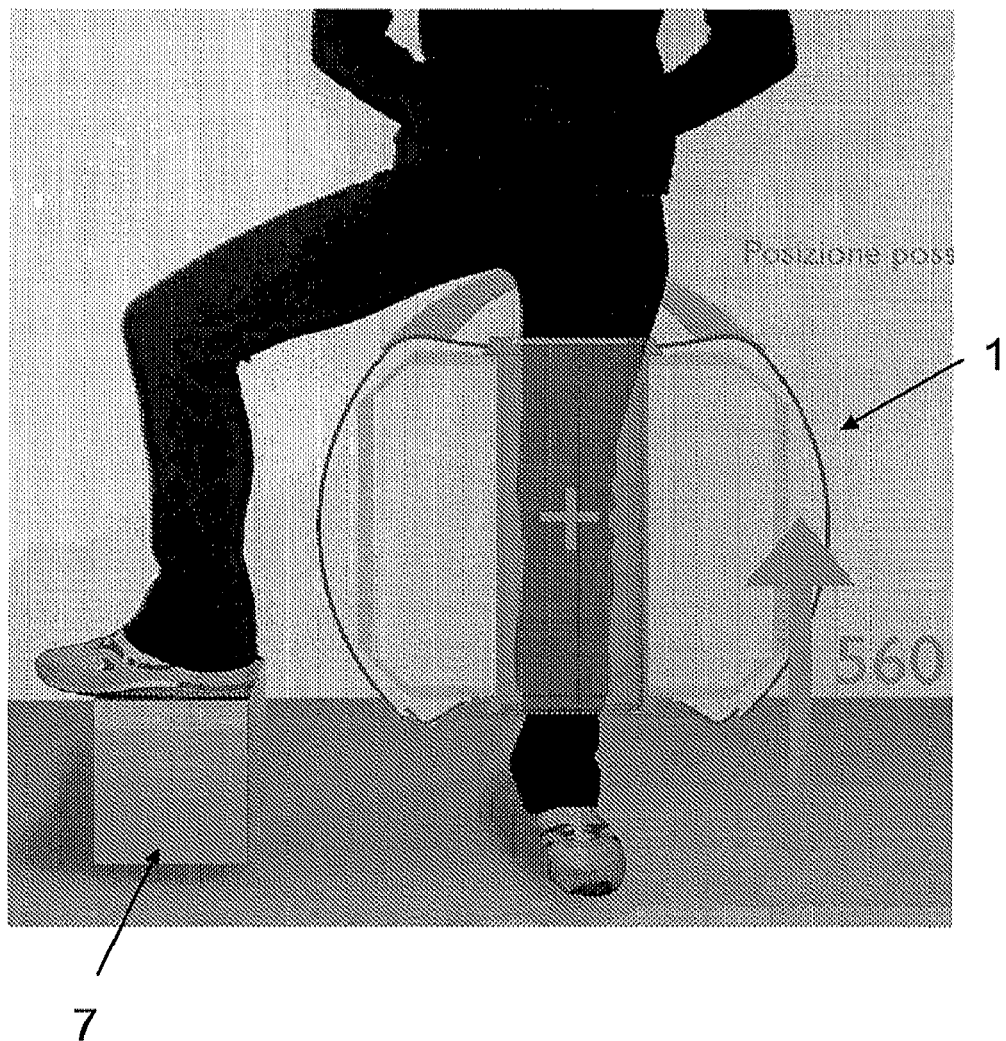
FIG. 3 is a diagrammatic view of an example of application of a magnetic structure as shown in the previous Figure to a patient that introduces a, lower limb therein while assuming a natural standing position with the limb to be imaged.

According to a first feature of the invention, which is particularly shown in FIG. 2, the direction of insertion of a body part, e.g. a lower limb, is a vertical direction from top to bottom. When the imaged part is a lower limb, as shown in FIG. 3, in the annular or toroidal structure 1 that delimits the cavity or chamber designed to receive one of the lower limbs, the wall on the side of the magnetic structure or of the scanner body oriented towards the second lower limb adjacent the former, here designated as wall 401 or 201 advantageously has a width or thickness smaller than the natural distance between the two lower limbs, or anyway such a size as to avoid the need of opening the limbs apart. This position would be incorrect, as the limbs would be inclined with respect to each other and to a vertical axis.

If the wall 401 or 201 cannot be formed with a thin or low-thickness design as shown in FIG. 2, then an arrangement can be provided allowing to position one of the lower limbs in the cavity of the magnet structure 1 without requiring the user to assume an uncomfortable posture. In this case, the external limb rests on a support 7 which is situated above the support plane for the lower limb within the cavity of the magnet structure, in such a manner as to provide an angled bent knee condition, with the upper portion of the lower limb substantially horizontal and the lower portion substantially vertical.

In this condition, the patient has a more comfortable position than with limbs opened apart and, still better, the relevant limb is oriented substantially parallel to the axis of the cavity or the annular shape of the magnet structure, i.e. in a proper imaging position.

This condition is shown in FIG. 3. It will be appreciated that the raised support 7 for the lower limb outside the closed annular or tubular magnet structure allows the lower limb to form a bridge structure passing over the peripheral wall of the annular structure 1, whereby the lower limb being imaged may be held in a proper vertical position, under proper stress conditions.

This embodiment allows to use a closed annular or tubular magnet whose cavity is only open and accessible at its end sides, for particularly imaging lower limbs of human beings and/or animals. Advantageously, the magnetic structure or scanner 1 may be positioned at various heights, so that different anatomic regions along the lower limb may be imaged, and the height position of the magnetic structure or scanner may be adapted to the different anatomies of different species.

Figure 15:
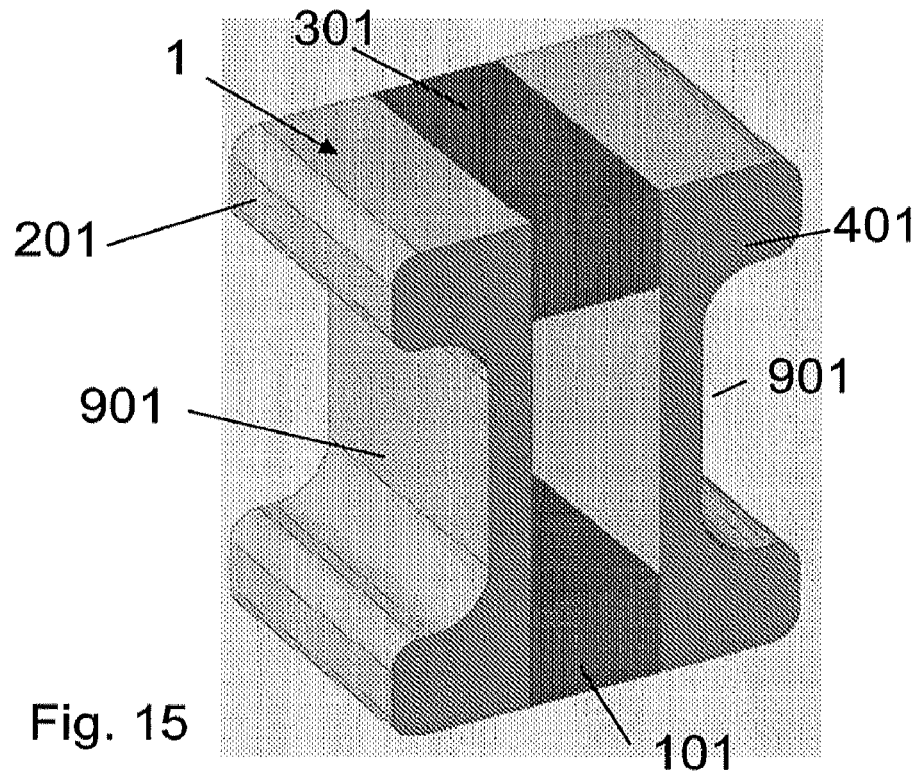
FIGS. 15 and 16 illustrate a square toroidal or annular scanner or magnetic structure delimiting a cavity or chamber having a rectangular cross section and being opened at two opposite sides perpendicular to the axis of the rectangular cross section.
Figure 16:
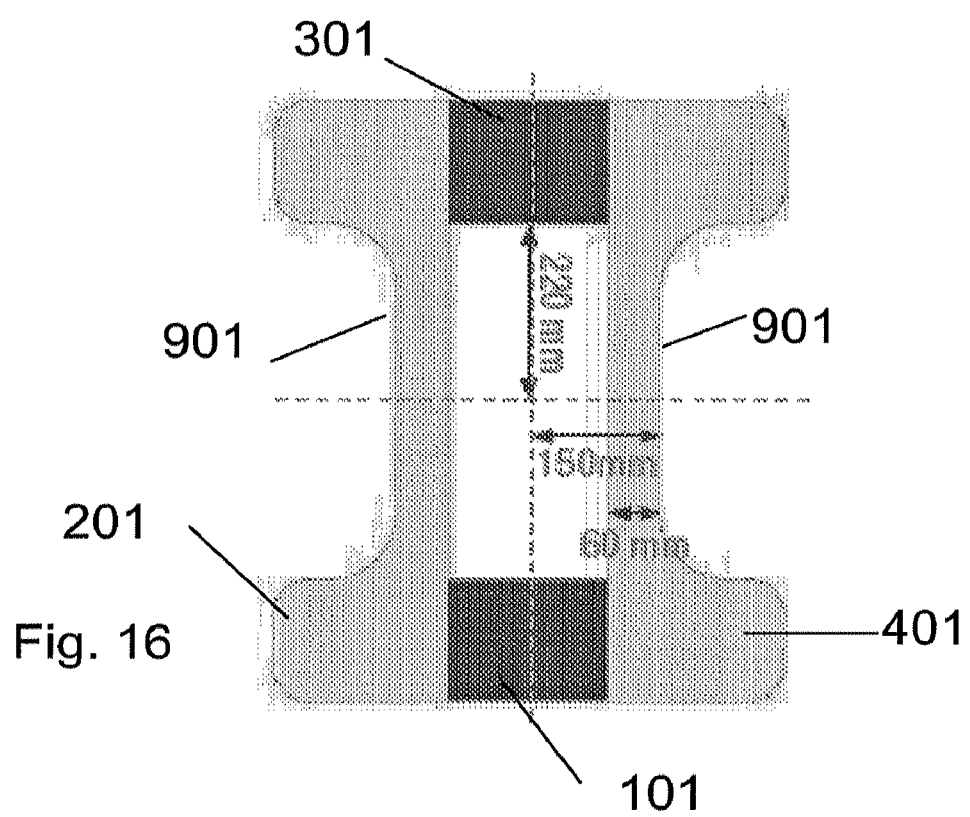

A further embodiment of the magnetic structure or scanner 1 is illustrated in FIGS. 15 to 29. Particularly FIGS. 15 and 16 illustrate a scanner 1 having an annular, rectangular cross section and delimiting a chamber C which has a rectangular cross section, is opened at two opposite ends and has a predetermined extension in the direction of the longitudinal axis which is perpendicular to the said open sides. In this embodiment the scanner 1 has on two opposite sides, particularly on the two longer opposite sides at the outside of the walls 201, 401 at the said longer opposite sides, and indentation 901.

Figure 17:
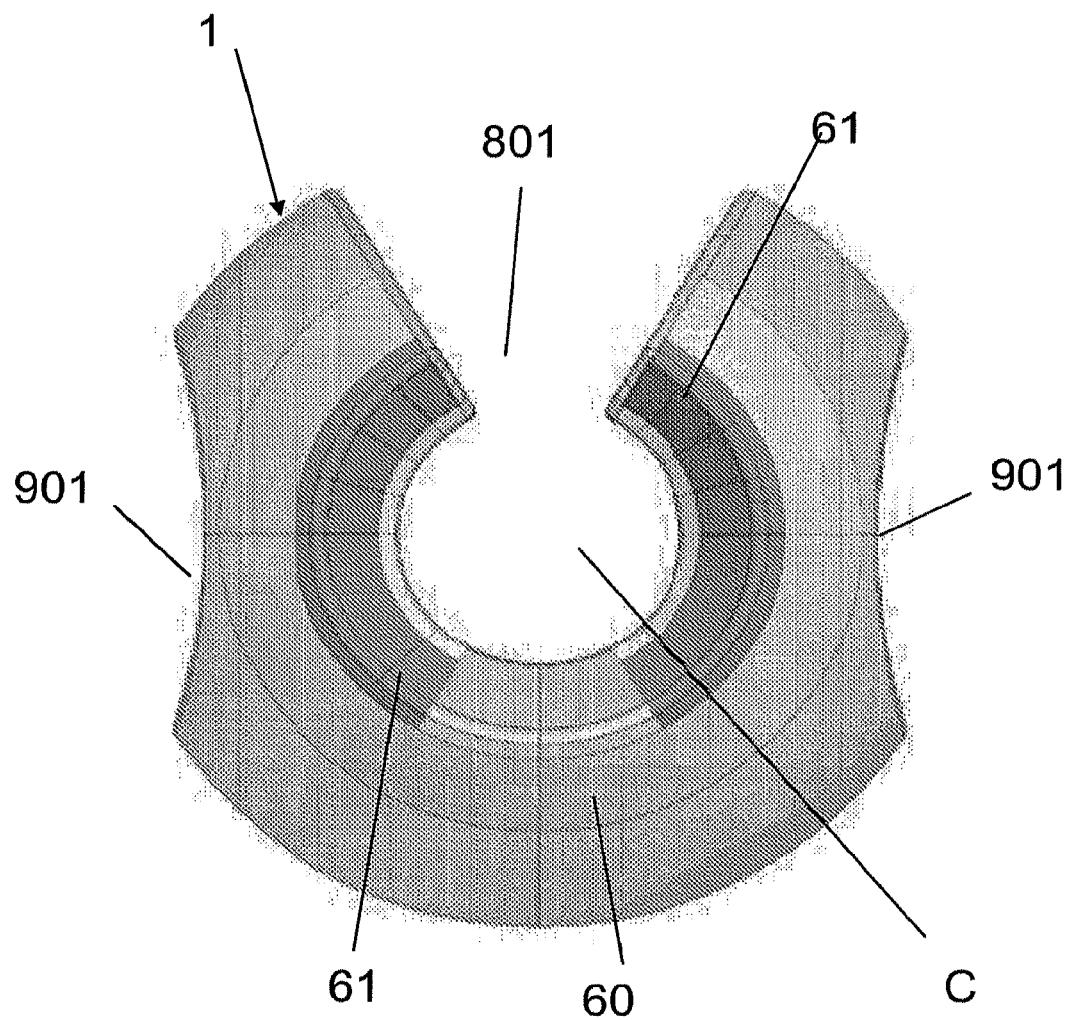
FIG. 17 illustrates a variant of the magnetic structure or of the scanner having a cylindrical or spherical shape and having a cross section which is in the form of an open ring, more particularly which has an extension less than 360° and which magnetic structure or scanner has two lateral indentations which are on diametrically oppose sides of the scanner and on both sides of the axial lateral opening.

Similarly in FIG. 17 the scanner illustrated therein has a cylindrical or spherical shape having a central cylindrical chamber C and the said scanner body having on two diametrically opposed side two external indentation 901.

This embodiment has the general advantage that imaging occurs with the limb under natural stress. Furthermore, a natural posture is also assumed or constructed during imaging, with reference to the anatomy of a particular animal species or to human anatomy. Particularly when imaging lower limbs or relatively large-sized and heavy animals, this avoids the provision of animal positioning devices on which the animal has to be held by force, possibly under anesthesia. This reduces both the risks associated to anesthesia and the problems arising from the handling of large animal bodies under anesthesia, which would often require special equipment for supporting and handling large weights.

The embodiment that is shown and described in the previous Figures is relatively simple. The next Figures show several alternatives of a, particular embodiment in which at least one body part, such as an upper or lower limb, may be introduced in two different orthogonal directions, particularly in a vertical insertion direction and a horizontal insertion direction.

In this case, the invention proposes that the magnetic structure or the scanner of a magnetic resonance imaging apparatus be positioned with the axis A of the open or closed annular or tubular shape of the magnetic structure tilted 45° with respect to the vertical or horizontal position.

Figure 4:
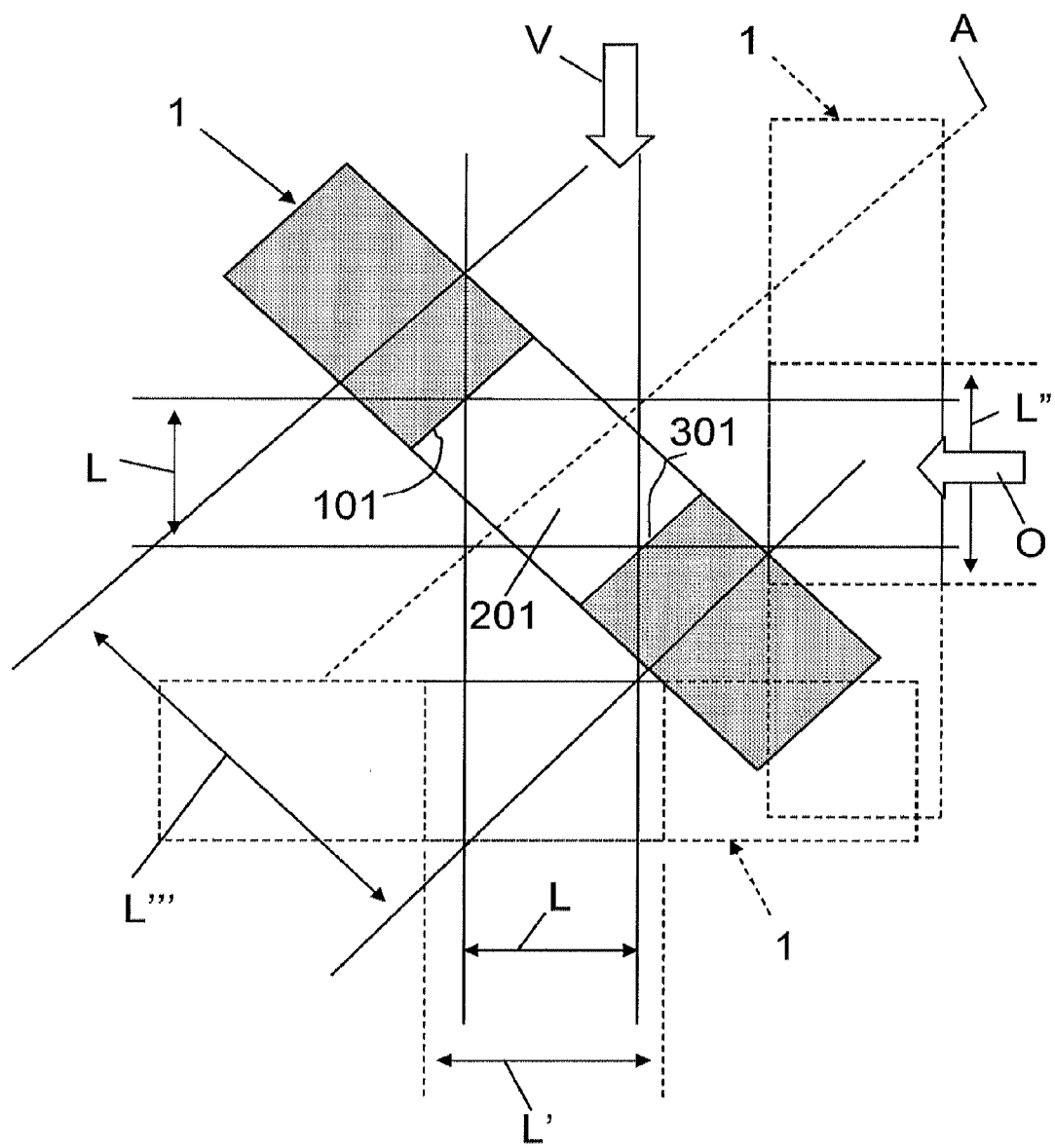
FIG. 4 is a view related to a condition in which the magnet as shown in the previous FIGS. 1 and 2 has the axis of its annular shape tilted 45° with respect to the vertical or horizontal direction, which indicates the required size of the central opening of the annular shape to obtain the same passage opening in such tilted condition as in the horizontal or vertical condition, with the patient being introduced in a horizontal or vertical position, as shown by arrows V and O.

FIG. 4 shows the ratio of the useful span or passage opening size L for insertion of a body in a cavity of a closed annular magnetic structure 1 having a rectangular plan shape when such structure is disposed with its axis tilted 45° with respect to the horizontal or the vertical and with an axis of rotation perpendicular to two of the four sides 201, 401 and parallel to the other two sides 101, 301, to the passage opening sizes L' and L" when such magnetic structure is disposed with the axis of the annular shape oriented vertically and horizontally and the insertion direction is accordingly a vertical and a horizontal direction respectively.

As shown in FIG. 4, the opening size L corresponding to the condition in which the annular magnetic structure 1 has no axial extension is smaller than the opening sizes L' and L" which, in the horizontal and vertical positions of the magnetic structure 1, correspond to the plan shape size of the open end sides of the cavity delimited by the inner shell walls 101, 201, 301, 401. However, considering that the magnet structure 1 has an axial extension d, the sizes of the open sides of the 45° tilted magnet structure required to assure the same passage opening size L increase considerably to L''', whereas, when maintaining the sizes of the open sides of the cavity unchanged, the passage opening size L dramatically reduced to L"".

Figure 11:
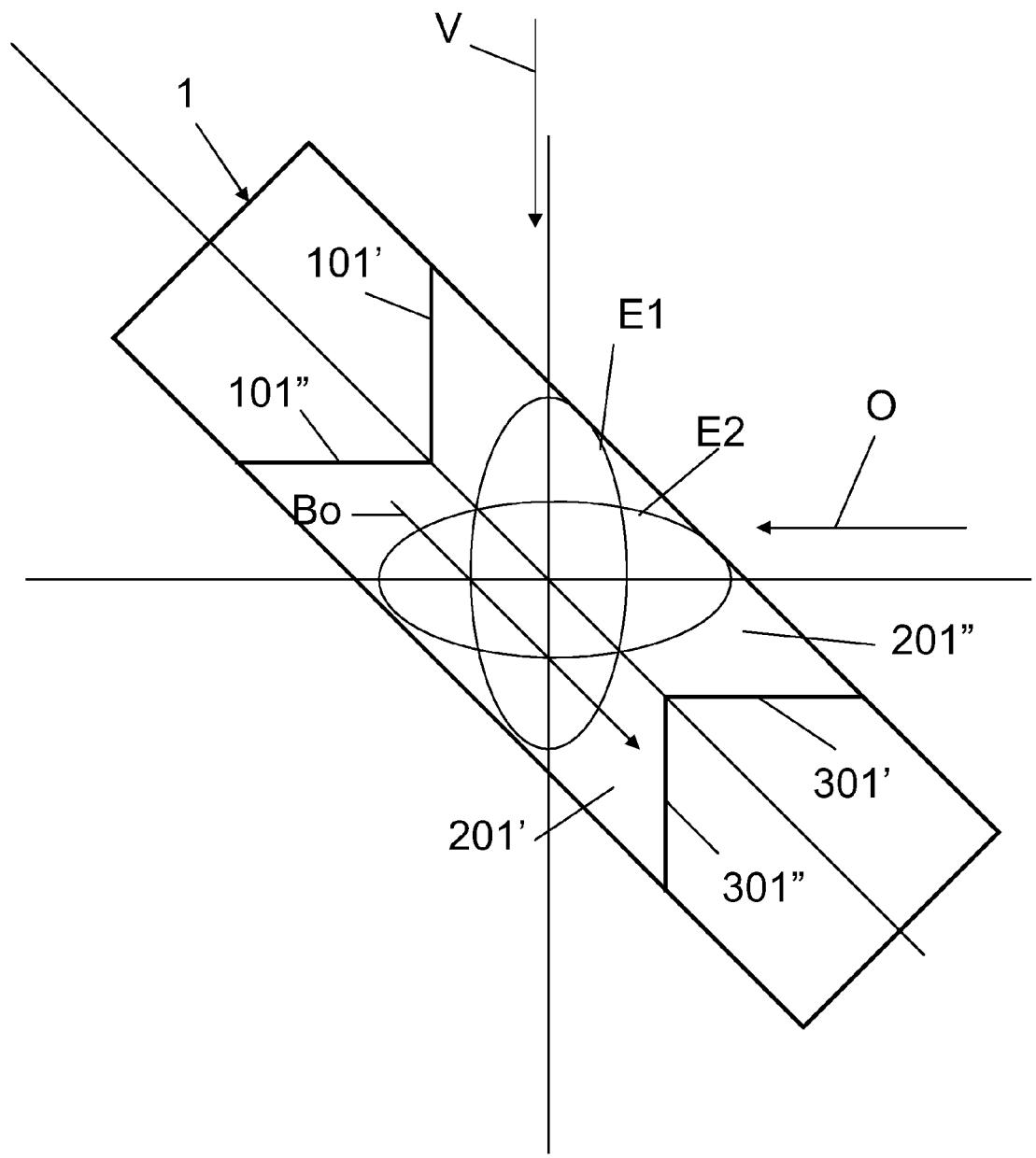
FIG. 11 is a view of a further variant of the annular magnet structure in which the magnetic field is optimized within an ellipsoid, with alternate vertical and horizontal longer axes, as taken in the same section as FIG. 7.

A first arrangement suggested by this invention to avoid the use of an oversize magnetic structure or scanner while providing a sufficient passage opening size and an optimized magnetic field for MR imaging includes providing that the inner shell walls of the annular magnet structure 1 be formed with a 45° inclination with respect to the axis of the annular shape, with two orthogonal orientations of the two sections of inner shell walls 101', 201', 301', 401' and 101", 201", 301", 401", extending on both sides of a median plane perpendicular to the axis of the annular shape of the magnet structure 1 (see FIG. 11).

When, like in the illustrated example the magnet structure 1 has an annular rectangular or square shape, with two shell walls 101, 301 parallel to the axis about which the structure is tilted, then the above shape need only be provided for said two opposite inner shell walls 101, 301.

Figure 5:
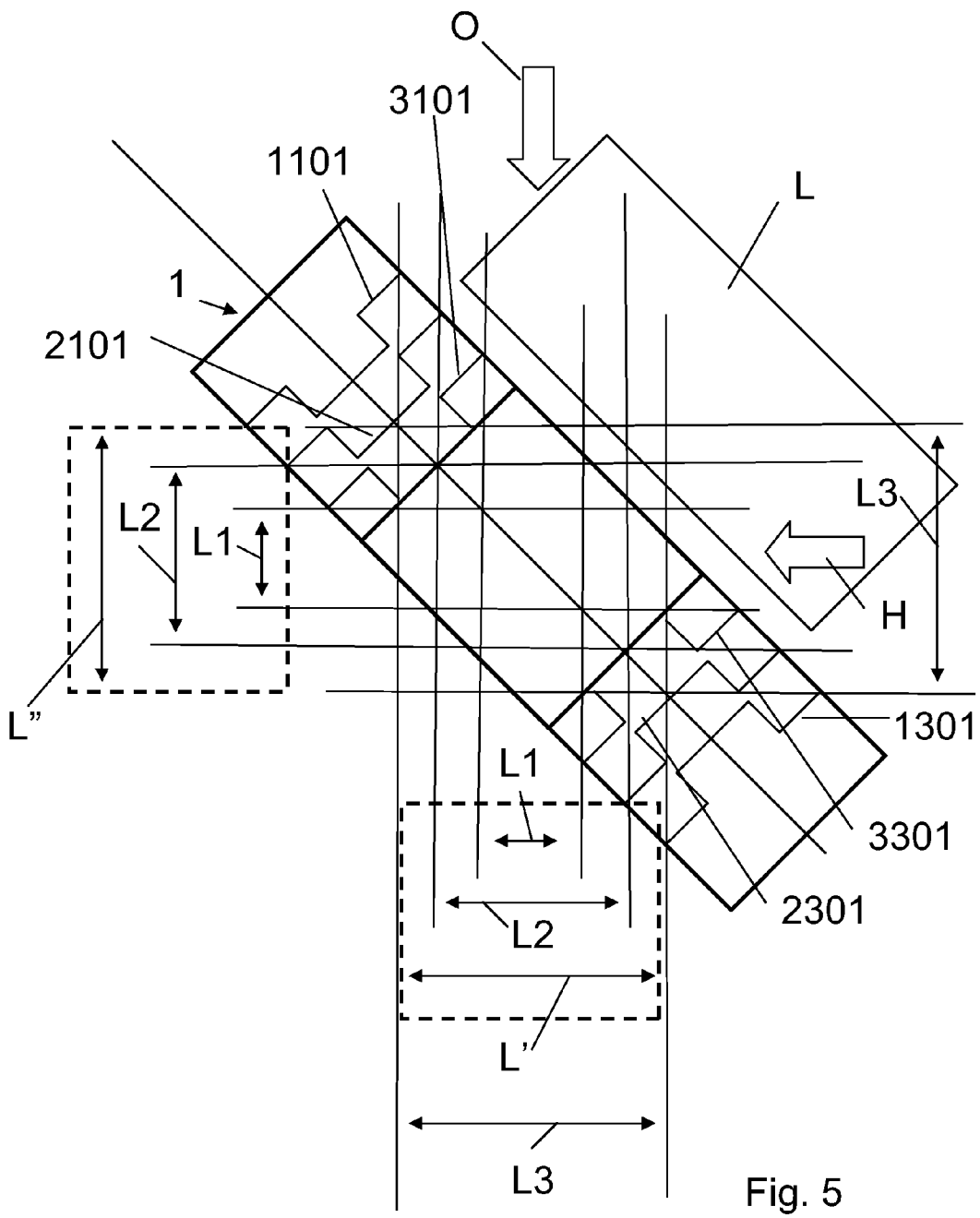
FIG. 5 is a diagrammatic view of a compromise solution to optimize the vertical and horizontal passage opening size in the condition of the annular magnet structure with a 45° tilted axis as shown in FIG. 4, and the magnetic field required for imaging.

This condition is shown in FIG. 5. In this case, the two inner shell walls 101, 301 are also the walls that support or form the means for generating the static field Bo and the inclined walls are approximated by a stepped structure.

The stepped structure may be composed of two or more steps, having such sizes that the apices of the steps are tangent to the ideal envelope surface of the inner shell walls 101, 301 which delimit the cavity for receiving the body or body part to be imaged on diametrically opposite sides.

In FIG. 5, the walls 101 and 301 include one central step. The sectional shape, as taken in a vertical plane perpendicular to such walls 101, 301 is shown in various positions with respect to the center axis, and is designated by numerals 1101, 2101, 3101 and 1301, 2301 and 3301.

For each of these positions, a passage opening size L1, L2, L3 is indicated for both insertion directions designated by arrows V and O. Furthermore, these introduction opening sizes are shown in comparison with the passage opening sizes L' and L" that would be provided by the magnet structure in the horizontal and vertical positions. The rectangle L shows the cavity size that would be obtained with the walls in the positions 3101 and 3301 corresponding to the passage opening size L3.

Figure 6:
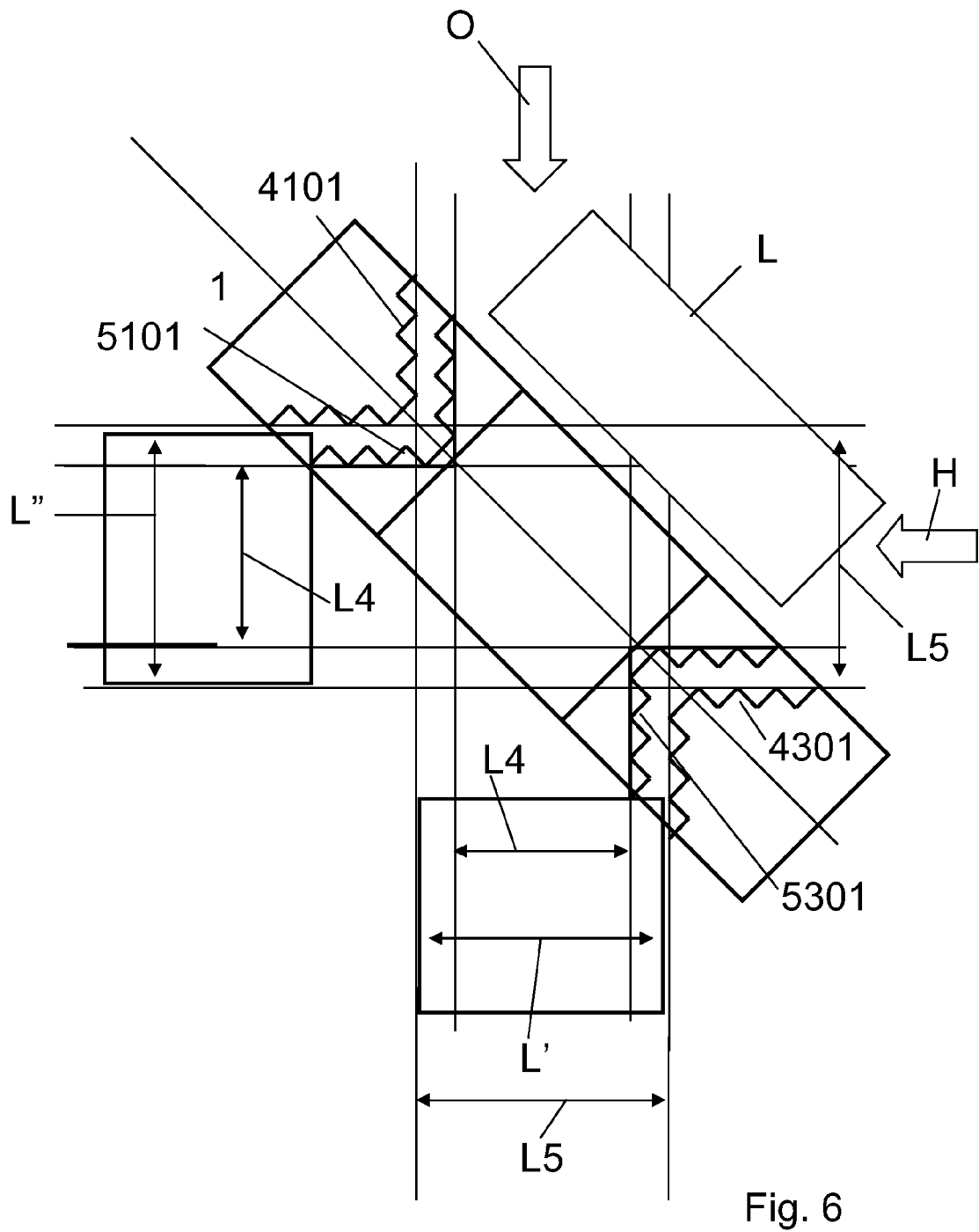
FIG. 6 shows a variant of the embodiment of FIG. 5.

FIG. 6 shows the same conditions as above for a different configuration of the walls 101 and 301, which have a greater number of steps. Here only two positions of the walls are shown, which are designated by 4101, 5101 and 4301, 5301, whereas their respective passage opening sizes L4, L5 are compared with the passage opening sizes L' and L" that would be obtained with the magnet structures in the horizontal and vertical positions. Once again the rectangle L denotes the cavity size that would be obtained with the walls in the positions 5101 and 5301 and with the passage opening size L5.

Figure 7:
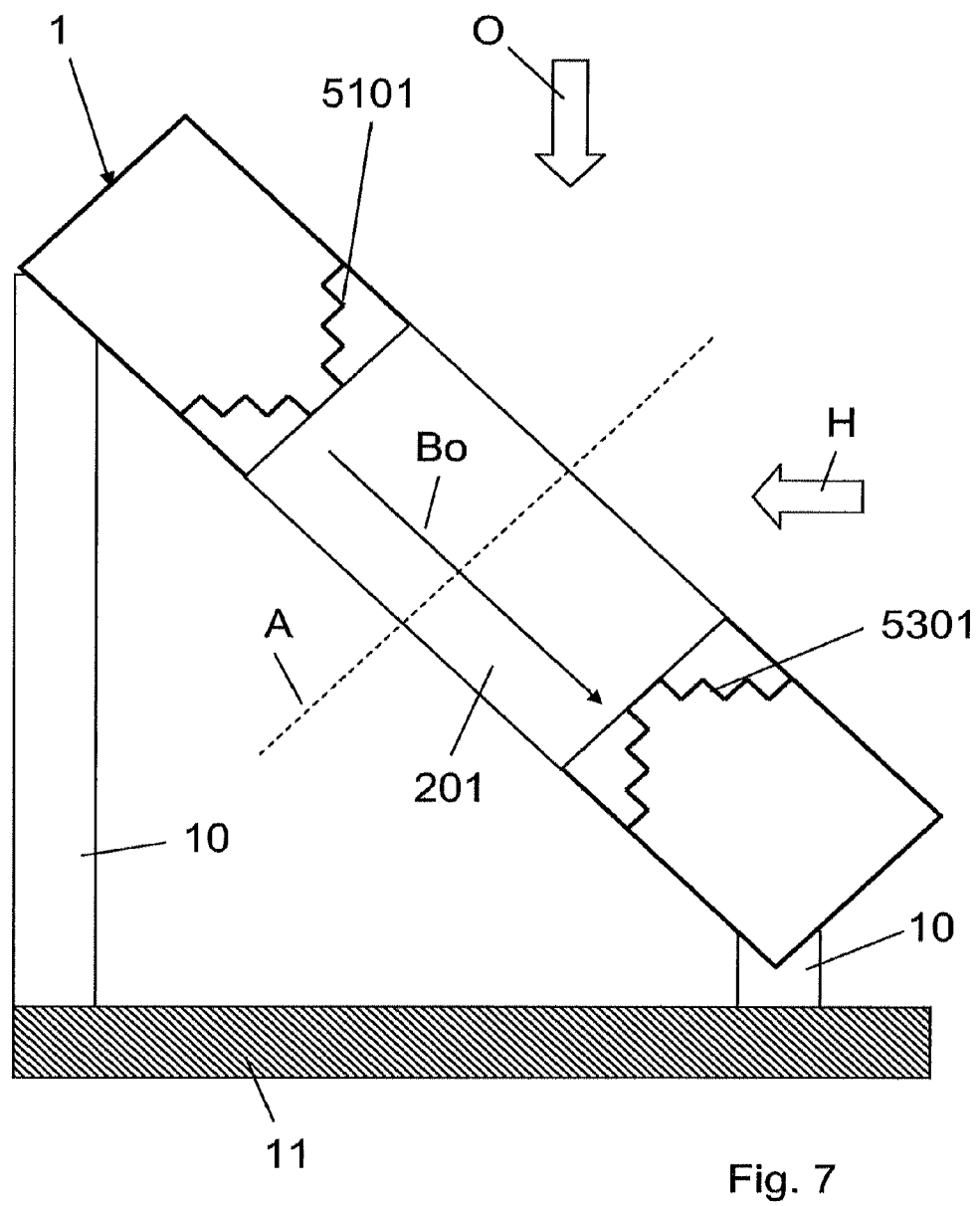
FIG. 7 is a diagrammatic view of a section of an annular magnet structure as shown in FIG. 6, as taken in a vertical plane perpendicular to the annular structure walls that support or form the magnetic field generating means, with the means for supporting it.
Figure 8:
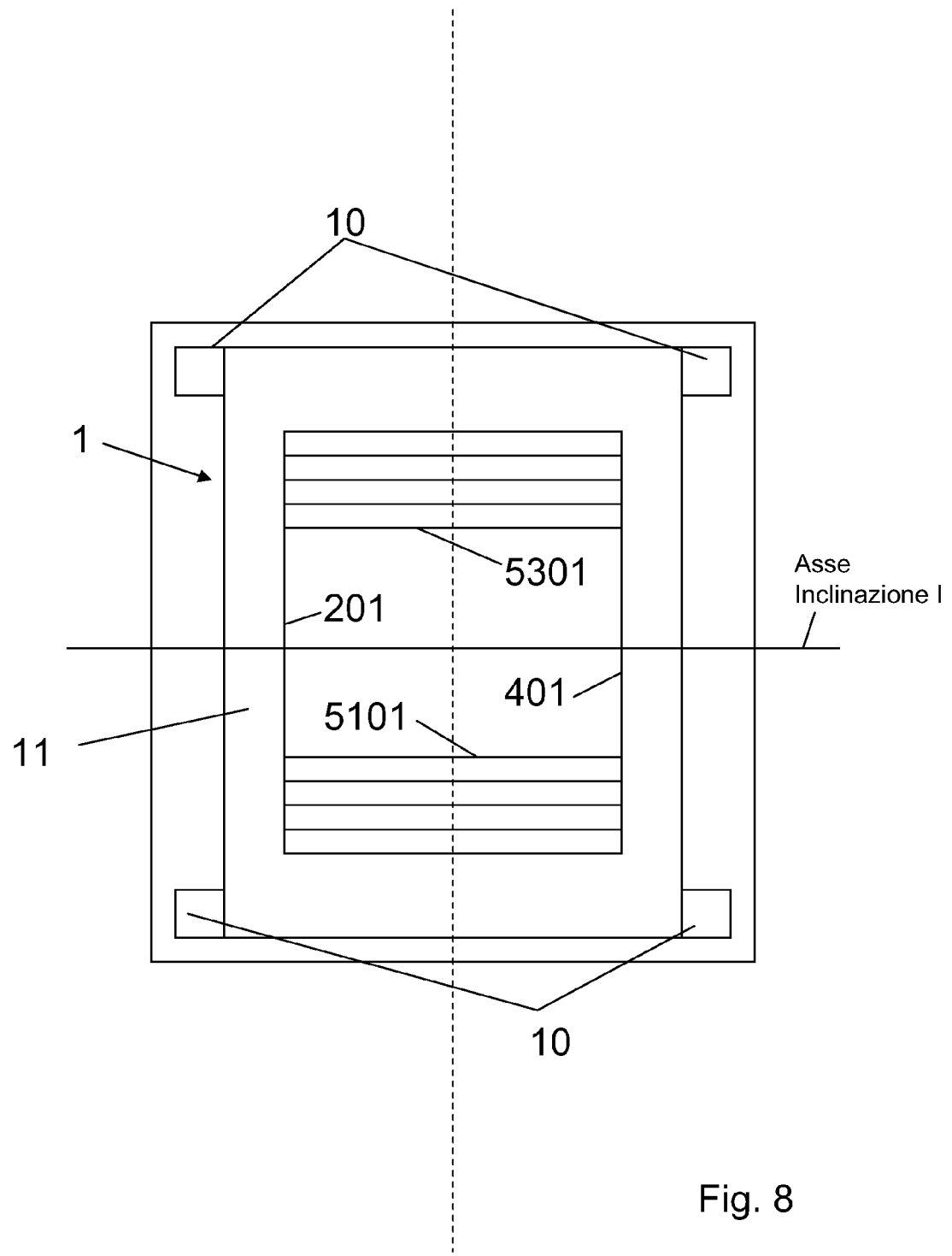
FIG. 8 is a, plan view of the magnet structure of FIG. 7, in which the section plane of the previous

FIGS. 7 and 8 show more schematically a magnet structure according to the example of FIG. 6, in which the structure is held in a tilted position with the axis of the annular shape oriented at an angle of 45° with respect to the vertical or horizontal direction of columns 10 fixed to a base 11. While the columns 10 are shown as stationary elements, they may be also extensible in length and form guides for vertical translation of the magnet structure 1 to allow height adjustment thereof.

The walls 101, 301 may be the walls that support, hold or form the means for generating the magnetic field Bo.

In this case, advantages are obtained by the use of a structure formed with steps or oppositely inclined wedge-shaped surfaces of said inner shell walls 101, 301 of the annular magnet structure 1 to optimize the magnetic field by a particular configuration of the magnetic field generating means.

For this purpose, the teaching of patent application EP 921 408, by the owner hereof, is used herein. According to this teaching, a permanent magnet for magnetic resonance imaging which comprises a magnet structure having a yoke and magnetic pole pieces, so shaped as to delimit or enclose a cavity, at least part of whose volume forms a compartment for receiving at least part of a body to be imaged and at least part of whose volume is the volume permeated by a static field having specific strength and homogeneity and wherein the magnet structure has at least one open side, parallel to the static field, may have an optimized magnetic field between two opposite facing pole pieces transverse to the open side between which the static field is generated when, at the open side/s, the magnet has means for correcting the static field generated by the main pole pieces, which correcting means increase the magnetic potential at the opening and over a predetermined depth transverse to the open side, without limiting the opening size.

Particularly, at the open side/s, there are provided two opposite auxiliary pole pieces, which extend inwards over a predetermined distance towards their respective main pole pieces, magnetized material being associated to such auxiliary pole pieces using two alternative or combined methods, which consist in that the magnetized material associated with the auxiliary pole pieces is in greater quantity and of different quality with respect to the magnetized material associated with the main pole pieces, in such a manner as to obtain an increase of the magnetic potential in the area between said auxiliary pole pieces with respect to that between the main pole pieces, and/or the magnetized material associated with the auxiliary pole pieces is equal as regards quantity and type to the magnetized material associated with the main pole pieces, whereas a magnetized insert is interposed between the main pole piece and the adjacent auxiliary pole piece, so as to generate an additional magnetic potential difference between the main pole pieces and the adjacent auxiliary pole pieces, and to increase the magnetic potential of the auxiliary pole pieces with respect to the potential of their respective main pole pieces. These two arrangements are provided while keeping the distance between the pairs of opposite auxiliary pole pieces at least equal to, or greater than the distance between the main pole pieces, or the auxiliary pole pieces are provided at a step-like widened area of the opening or the opening size for access into the cavity.

Figure 9:
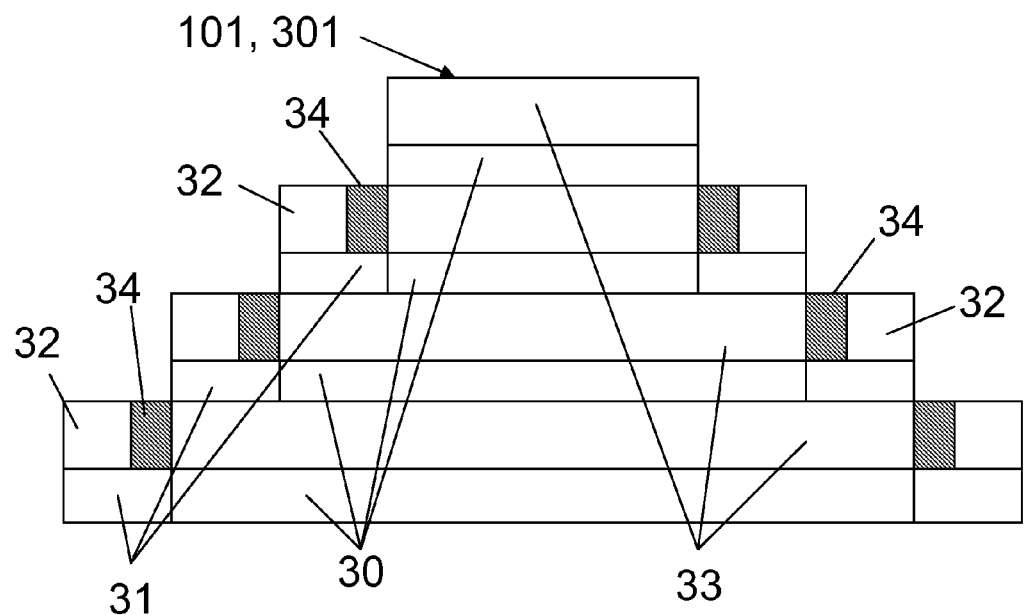
FIG. 9 is a diagrammatic cross sectional view of a first embodiment of the magnetic field generating means, in the form of permanently magnetized material, as taken in the same plane as FIG. 7.

The above construction combination of the pole pieces is shown in greater detail in FIG. 9. Particularly, the magnetic field generating means are magnetic pole pieces located at the inner shell walls 101 or 301 which are oriented parallel to the axis of tilt of the magnet structure 1 or form such walls. These pole pieces include combinations of permanently magnetized elements and non magnetized metal elements.

FIG. 9 shows a pole piece having a stepped surface which is adapted to form an inner shell wall 101 or 301, and has, at its base, a first central plate of magnetized material 30, laterally extending by two elements of magnetized material 31, whereas the layer of magnetized material 30 is covered with a layer of ferromagnetic material 33 or having a predetermined permeability and the elements 31 are covered with an end element 32 of ferromagnetic material or having a predetermined permeability, a magnetized element 34 being interposed between the latter and the layer 33.

This structure is also provided for the next steps up to the last central step, which is preferably only composed of the layer of magnetized material 30 and the layer of ferromagnetic material or having a predetermined permeability 33.

Still according to the teaching of patent application EP 921 408, whose content is hereby incorporated by reference, the various magnetized inserts may have preferred magnetization vector directions and particularly the layers of magnetized material 30 and 31 may have parallel magnetization vectors, whereas the magnetized insert 34 has a magnetization vector with at least one component perpendicular to the magnetization vectors of the layers 30 and 31 or perpendicular thereto, and oriented, for instance, towards the central layer 30.

Thanks to this construction of the magnetic field generating means, outward bowing of the magnetic field lines near the open end sides is dramatically reduced, and the access opening may be also increased, in terms of sizes of either the access opening or the open side of the magnet structure.

As disclosed in patent EP 921 408, the combination of layers of magnetized material and ferromagnetic material or material having a predetermined permeability is not limited to the one illustrated above, but may vary depending on the performances required of the magnet structure, both in terms of size and in terms of properties of the magnetic field and the imaging volume.

Figure 10:
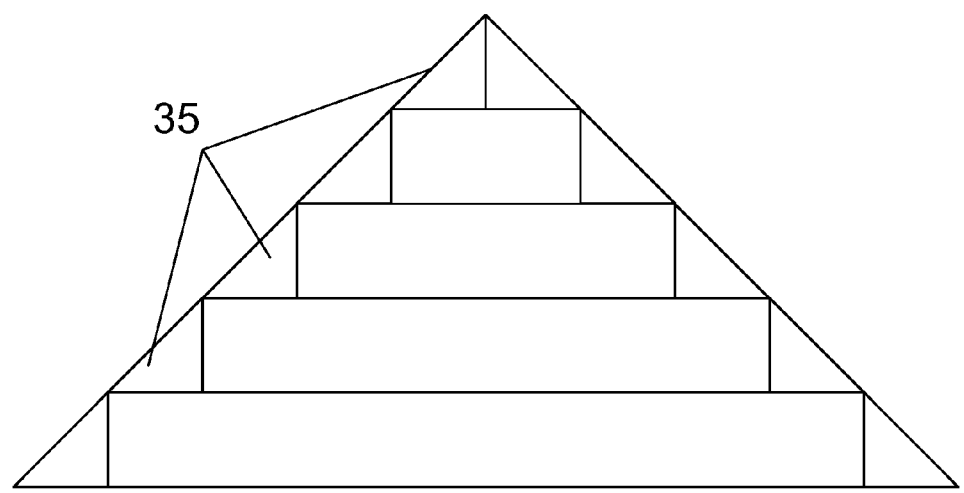
FIG. 10 shows a variant of the embodiment of FIG. 9.

As shown in FIG. 10, the magnetic field generating means shall not necessarily be formed of surfaces designed to form the inner shell walls 101 and 301 of the stepped magnet structure 1, but these surfaces may also have flat shapes and form the envelope surfaces of these step-like surfaces. Here, magnetized or non magnetized elements 35 may be provided, which have a triangular section and complete the steps between the various layers of material that form the magnetic field generating means.

FIG. 11 diagrammatically shows a magnet structure in which the magnetic field generating means are provided along the two opposite sides that form the inner shell walls 101 and 302 of the annular or tubular structure and are formed according to the example of FIG. 10.

According to a further feature, FIG. 11 shows two ideal elliptical surfaces within which the magnetic field is optimized by shimming.

Ellipsoidal shimming may be carried out as disclosed in:

As is apparent from such description, by selecting a particular ellipsoidal surface E1, E2, the region in which the magnetic field has the required or desired characteristics may be extended in the direction of the axis of introduction of the body or the part thereof to be imaged. Particularly, this is obtained by defining an ellipsoidal surface whose longer axis is oriented in such direction of introduction.

Figure 13:
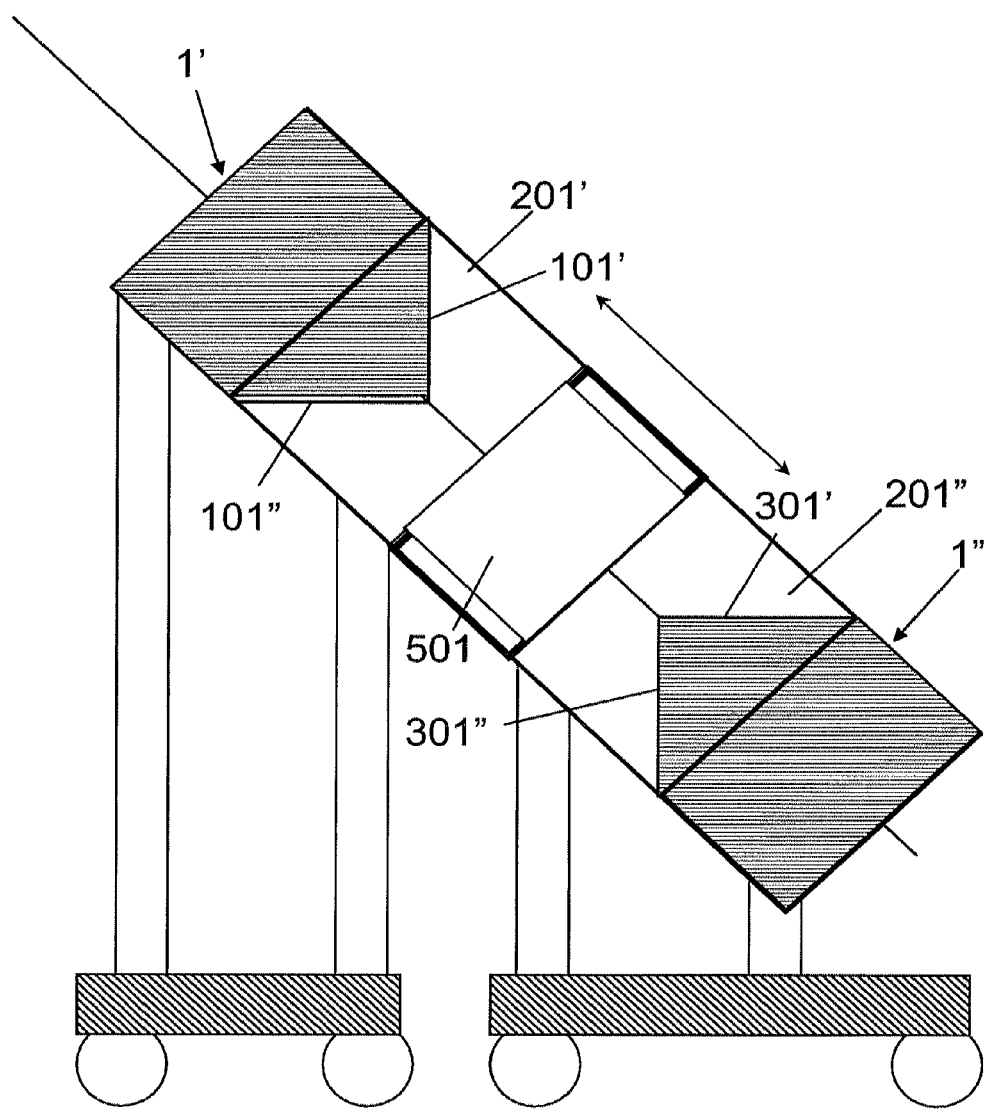
FIG. 13 shows a further variant embodiment in which the annular structure is extendable in the longitudinal direction of the walls perpendicular to the walls that form or support the magnetic field generating means and/or are parallel to the axis of tilt.

FIG. 13 shows another variant in which the magnetic structure is extensible in a direction perpendicular to the two inner shell walls 101 and 301 which support or form the static field generating means.

In this case, the magnet structure is formed of two semi-annular parts 1', 1", which are connected together by extensible members.

According to yet another feature, each semi-annular element 1', 1" is supported by a separate wheeled carriage-mounted bearing structure which allows the two half-rings 1', 1" to be drawn toward and away from each other.

The means for relative displacement of the two semi-annular elements of the magnet structure, which can extend and/or shorten the sides of the magnet structure that form the inner shell walls 201, 401 and cause the inner shell walls 101, 301, with the magnetic field generating means associated thereto, to be drawn toward and away from each other, may be of any type, as selected by those skilled in the art among known and available means, such as mechanical, hydraulic or pneumatic means. For example, two double-acting hydraulic or oil cylinder actuators may be provided between the two semi-annular elements 1', 1", respectively interposed and aligned parallel to the two branches of the semi-annular elements 1', 1" designed to form the sides parallel to the inner shell surfaces 201 and 401, which actuators are held in the length adjustable tubular element 501 as shown in FIG. 13. The two cylinders may be controlled by a single source of pressurized fluid to always allow displacement of the two semi-annular elements 1', 1" parallel to themselves.

The movement of the magnetic field generating means towards and away from each other obviously has an effect on the characteristics of the static magnetic field wherefore, in combination with a magnet structure as shown in FIG. 13, there may be provided magnetic field generating means that can be adjusted by adding or removing magnetized elements and/or elements having a predetermined permeability from a base set of such elements, that forms a base configuration of the magnetic field generating means.

In all illustrated embodiments, including the one of FIG. 12 that will be described in greater detail hereafter, the magnetic field generating means may be resistive or superconducting magnets. Combinations of magnetic field generating means consisting of permanent magnets or resistive or superconducting magnets may be also provided.

This configuration of the magnetic field generating means, in which all the above means are composed at least partly of elements having a permanent magnetization and resistive or superconducting magnets allows to easily adapt for instance the magnetic field of the magnet structure as shown in FIG. 13 to the various selected sizes without adding or removing integration elements. In this case, it is only needed to turn on or off predetermined auxiliary electromagnets and/or adjust the magnetic field generating currents to obtain the desired field corrections. Here, the field generating means having a permanent magnetization may form the base configuration of the magnetic field generating means, i.e. to fit the minimum magnet structure size.

Analogously, a mixed configuration of the magnetic field generating means including permanently magnetized elements and resistive or superconducting magnets also allows to easily and quickly shim the magnetic field in different ellipsoids as needed. In this case, a predetermined configuration of shimming electromagnets may be provided for a certain number of predetermined different ellipsoids E1, E2 having different orientations in space and/or different sizes, which electromagnets have a predetermined position and a predetermined orientation. Therefore, information may be stored in a predetermined memory area for each ellipsoid, regarding which electromagnets have to be turned on and by which field generating currents to shim the magnetic field in a predetermined ellipsoid having a predetermined size and a predetermined orientation.

The user shall simply select the ellipsoid type within which the field has to be optimized for the control electronics of the apparatus to automatically set the shimming electromagnet parameters required for the selected ellipsoid.

This may be preconfigured upon fabrication of the magnetic resonance imaging apparatus.

Here again, a base configuration of the magnetic field generating means may be provided, in which such means consist of permanently magnetized material, whereas the resistive or superconducting magnets are only provided for optimization of the magnetic field, i.e. shimming of the magnetic field in the various selected ellipsoids.

Figure 12:
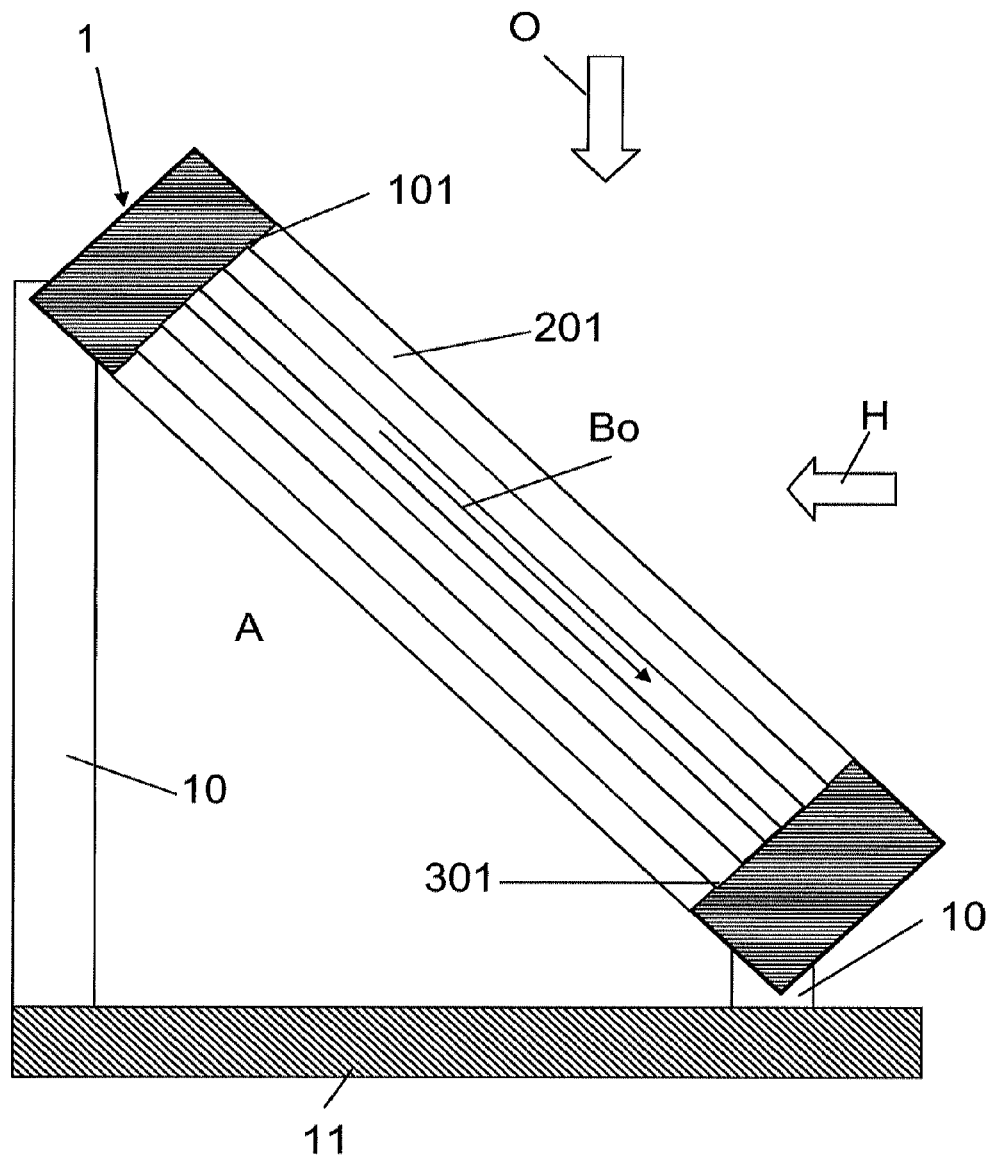
FIG. 12 shows a variant embodiment of an annular magnet structure in which the axis of tilt is perpendicular to the pair of walls that support or form the magnetic field generating means.

Regarding FIG. 12, here the magnet structure is tilted about an axis perpendicular to the inner shell surfaces 101 and 301 which form or support the means for generating the field Bo, which therefore is oriented parallel to this axis of tilt, unlike the previous examples in which the field Bo was perpendicular to the axis of tilt of the magnet structure.

Thanks to this arrangement, while the surfaces 101 and 301 may be formed exactly as described in the previous examples, the two sides that form the inner shell surfaces 201 and 401 have no magnetic field generating elements thereon and simply act as a yoke for reclosing the magnetic flux and further have the function to mechanically connect the two branches of the magnet structure that support the magnetic field generating means. Therefore, in this case, since the material has a sufficient permeability and a sufficient mechanical strength, these sides of the magnet structure 1 may be relatively thin, for instance having a thickness that is smaller than the distance between two adjacent lower limbs in human beings or animals of a certain size. This may allow a lower limb to be properly positioned in the cavity without opening the limbs apart, with the human or animal patient assuming a natural posture.

As mentioned above, the possibility for the patient to assume a natural position or posture is very important especially when the apparatus is used in veterinary applications, as the animal need simply be quiet or still for a short time, with no anesthesia or narcosis being required, therefore with no problem associated to support and handling of a narcotized animal, which problems are particularly serious when the animal has a very large size.

While the invention has been described with reference to a closed annular or tubular magnet structure, the above characteristics also apply to magnet structures having an open annular cross section or shape, such as a U- or C-cross section or such as the one illustrated in FIG. 17.

Figure 14:
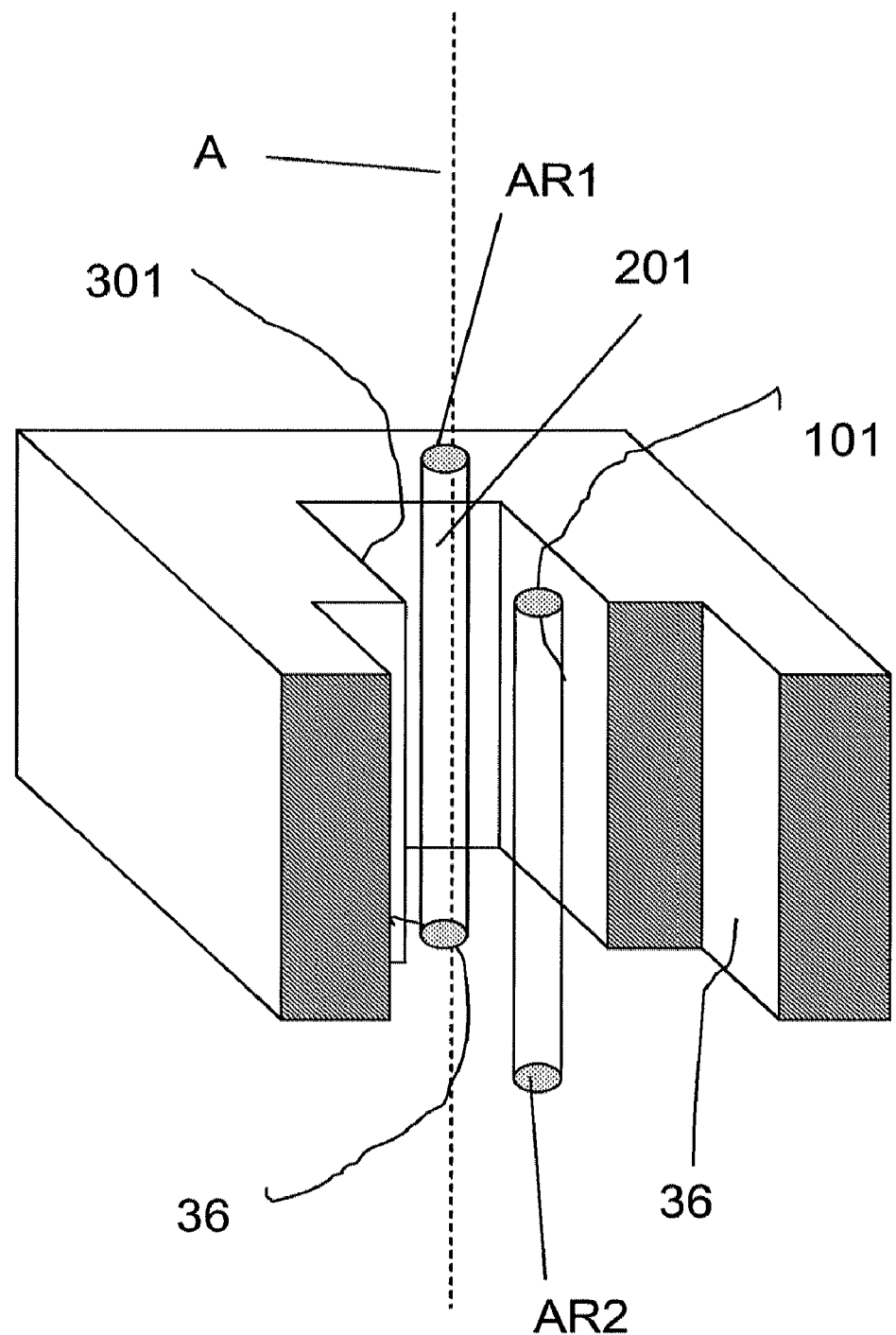
FIG. 14 is a perspective view of an open annular magnet structure, disposed with the axis of its annular shape oriented vertically, according to the present invention.

An embodiment of this kind of magnetic structure is also schematically shown in FIG. 14. The open U- or C-shaped annular structure, with one of the open sides, i.e. the one opposite the vertical side designated by numeral 201, oriented along at least one of the directional components of the static field Bo, the magnet structure is disposed with the axis A of the annular shape, i.e. the axis of the two opposite open end sides, oriented vertically, and with the open side parallel to one of the components of the magnetic field and to said axis. In this case, the magnet structure is oriented with said open side, which is parallel to the axis A of the annular shape, perpendicular to center-to-center distance between two adjacent lower limbs, indicated by the vertical cylinders AR1 and AR2 or to the plane subtended by two adjacent lower limbs. Therefore, when one of the two adjacent limbs is imaged, the other limb is in a comfortable natural position at the vertical open side of the magnet structure.

To increase comfort while reducing the size of the magnet structure, the U- or C-shaped magnet is formed with a flared or step-like enlarged configuration 36 at said vertical open side. This configuration may be obtained using one or more of the combinations disclosed in EP 921 408. In this case, the two walls 101 and 301 that form or support the static field generating means have a step-like widening 36 at a certain end strip on the open side of the magnet structure.

Alternatively or in addition, according to the invention at least one of the two walls that form the two opposite branches of the open annular structure which delimit the open side of the ring, has a thickness that is smaller than the lateral distance between the two limbs and the magnet is disposed with the axis of the open side of the open-ring structure oriented parallel or transverse to the lateral alignment axis of two adjacent lower limbs.

Referring again to FIGS. 15 and 16, the scanner illustrated therein is of the kind having a rectangular annular cross section defining a chamber having a rectangular cross section. Particularly the dimensions of the longer and shorter sides of the said chamber are indicated where the longer sides have approximately 440 mm and the shorter one approximately 180 mm. At the indentations 901 the walls have a thickness of 60 mm.

This kind of shape of the cross section of the cavity or chamber C allows to bend the limb at the knee or at the elbow depending if the limb is a lower or upper one. In this case the bent limb can fit inside the chamber since the increased volume occupied by it is ensured by the rectangular shape.

Similar conditions can be obtained in a cylindrical or spherical scanner according to FIG. 17. Here the chamber C has a cylindrical cross section but on one lateral side an opening 801 is provided which extends from one open end side to the opposite open end side of the chamber C. The scanner has so an open annular cross section or walls having an angular extension less than 360°. This opening may have a width which allows passage of the limb thus allowing to house at least partially a bent limb inside the chamber C at least at the level of the joint i.e. of the knee or of the elbow.

The two scanners according to FIGS. 15 and 16 and according to FIG. 17 may be used in different conditions and relative positions with reference to the patient body and to the patient posture.

Figure 18:
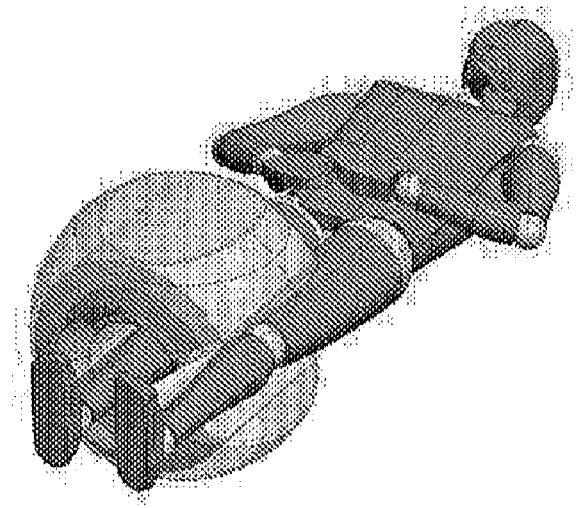
FIGS. 18 and 19 illustrate three different examples of relative position of the scanner or magnetic structure according to FIG. 17 the said structure having a different angular position relatively to the longitudinal axis of the chamber housing the limb and having different positions relatively to the longitudinal extension of the limb.
Figure 19:
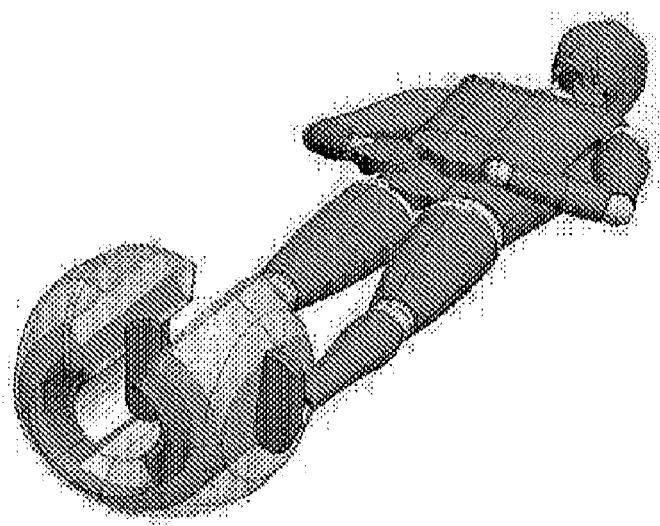
Figure 20:
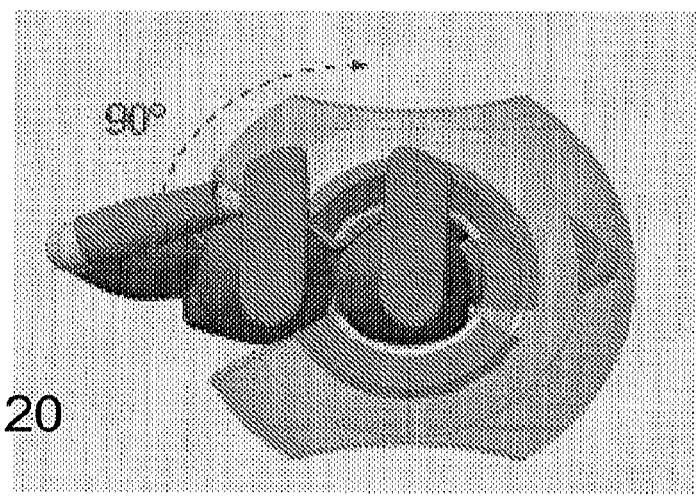
FIGS. 20 to 22 illustrate three positions of the scanner relatively to the limb having different angular positions relatively to the limbs and seen in direction of sight parallel to the longitudinal axis of the chamber of the scanner or of the magnetic structure.
Figure 21:
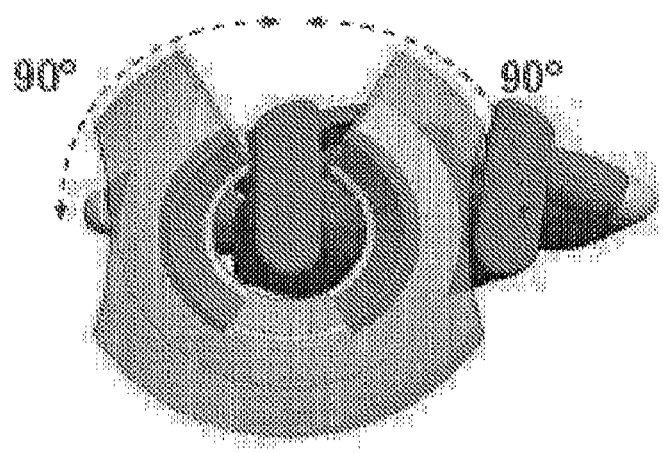
Figure 22:
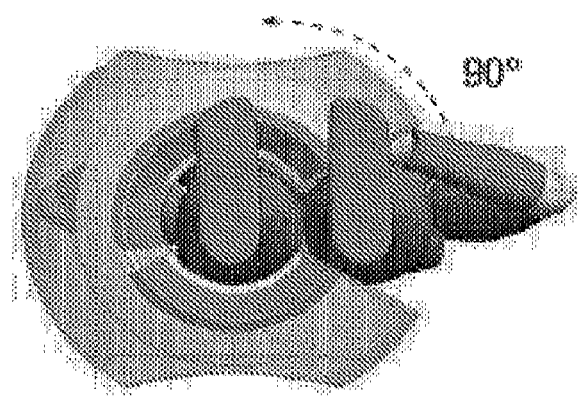

As illustrated in FIGS. 18 and 19 and in FIGS. 20 to 22, the patient may be in a lying posture while the longitudinal axis of the chamber is oriented horizontally. As illustrated by the said Figures, the scanner can be rotated around the horizontal longitudinal axis and thus around the limb of the patient. In these Figures, the relevance of the function of the indentations 901 and of the opening 801 appear clearly. Also the opening 801 can be used to reduce the distance of the two adjacent limbs, i.e. legs. This is obtained also by means of the fact that the ends of the scanner walls delimiting the said opening 801 are diverging one from the other in the direction away from the centre of the annular cross section.

As illustrated in FIGS. 18 and 19 displacing the scanner along the longitudinal axis of the leg allows to carry out imaging of the knee and of the foot. FIGS. 20 to 22 illustrate that the scanner 1 can be rotated around the limb to the left or to the right of 90°.

Figure 27:
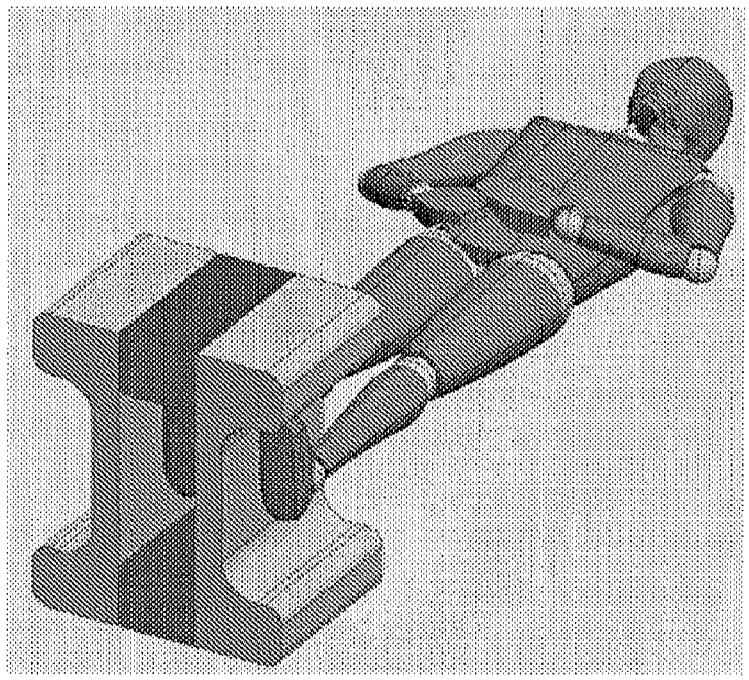
FIGS. 27 and 28 illustrate similar positions of the scanner and of the patient as in FIGS. 20 to 22 while the scanner is the one of FIGS. 15 and 16.
Figure 28:
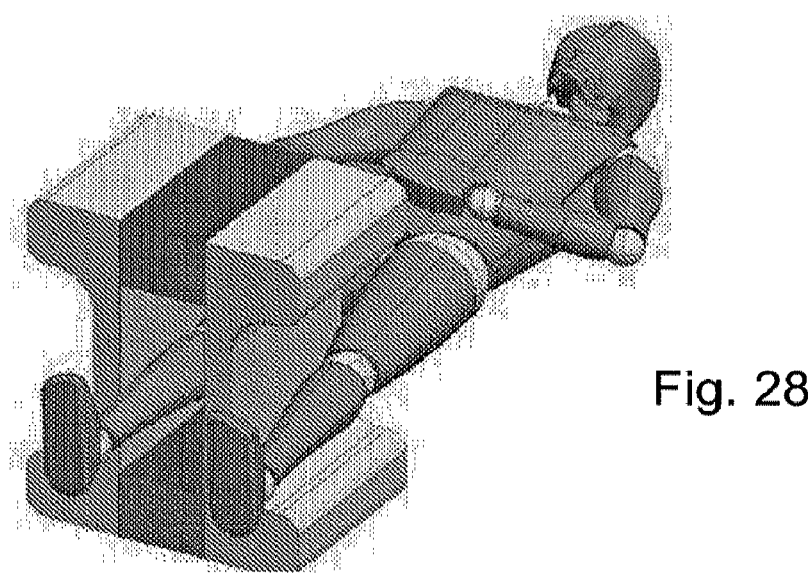
Figure 29:
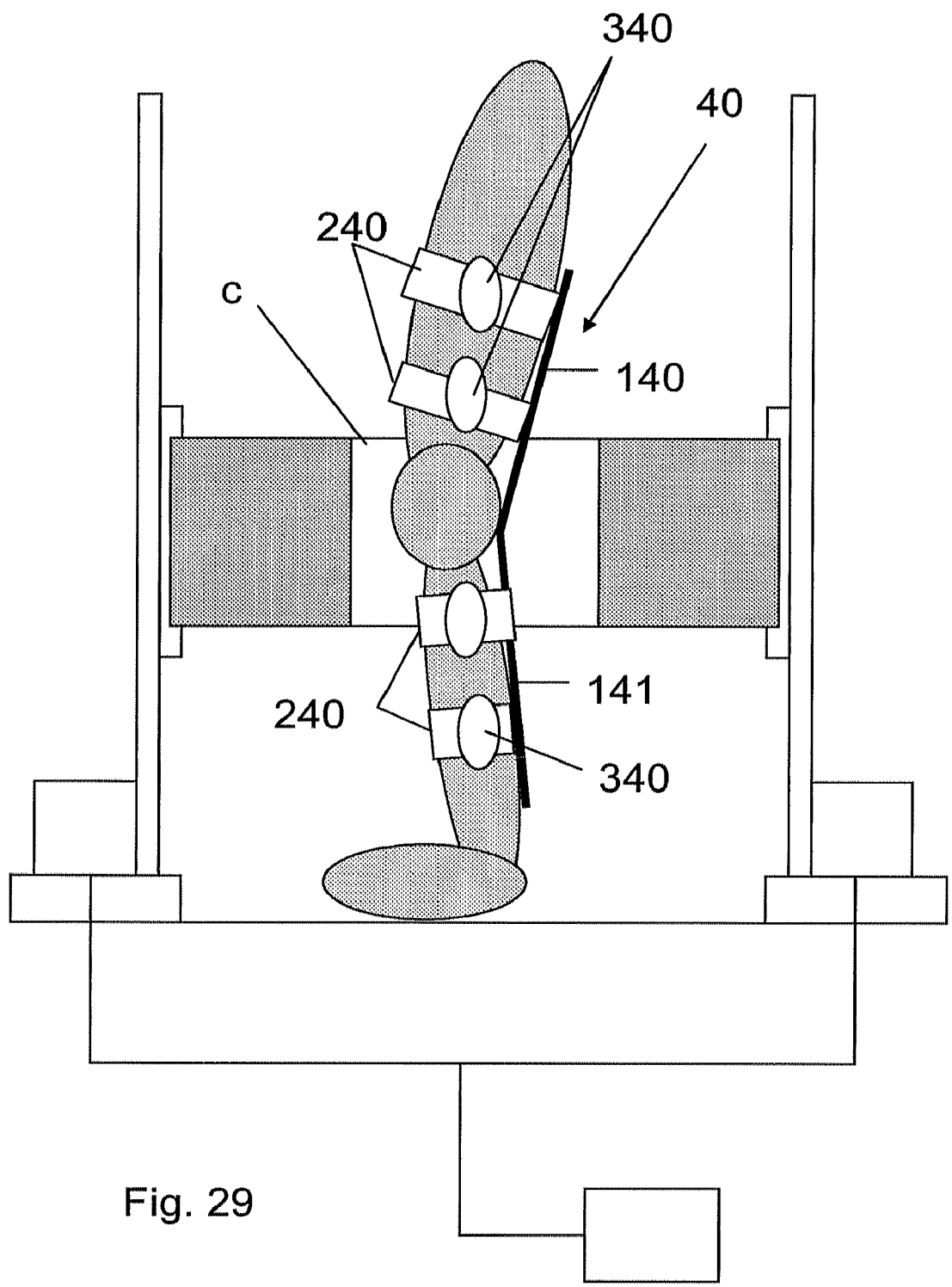
FIG. 29 illustrates in a schematic way the scanner according to FIG. 1 in combination with a device for blocking the leg in a predetermined posture.

Similar postures and relative position and orientations of the scanner according to FIGS. 15 and 16 relatively to the patient are illustrated in FIGS. 28 and 29. Here the patient is still lying and the chamber is also placed with its axis in an horizontal position, while FIG. 27 illustrates the scanner position relatively to the limb for imaging the foot and FIG. 27 illustrates the scanner position relatively to the limb for imaging the knee.

Figure 23:
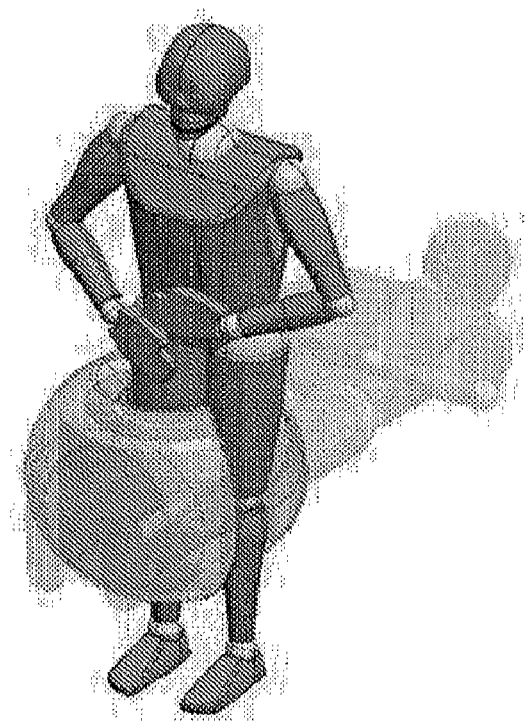
FIGS. 23 and 24 illustrate further two different relative positions of the scanner and of the patient, with the scanner of FIG. 17, in this case the longitudinal axis of the chamber housing the limb being vertical and the patient being in the upstanding position.
Figure 24:
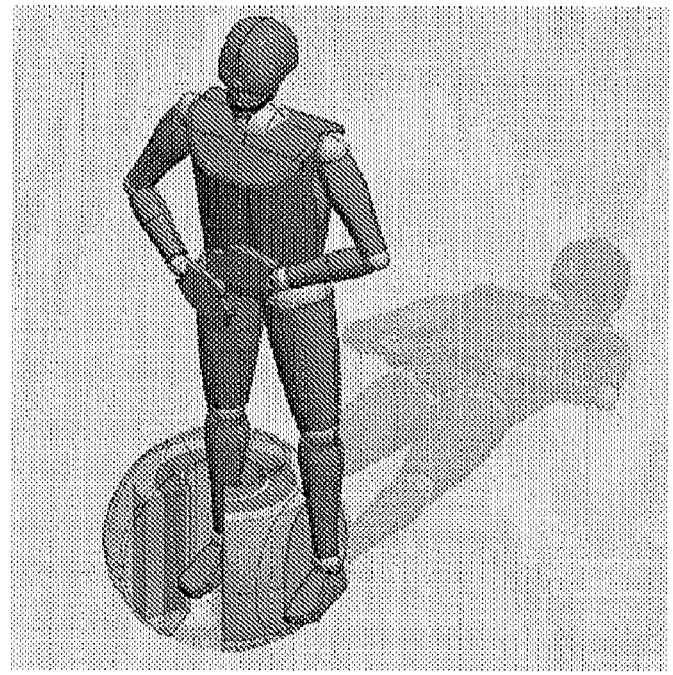
Figure 25:
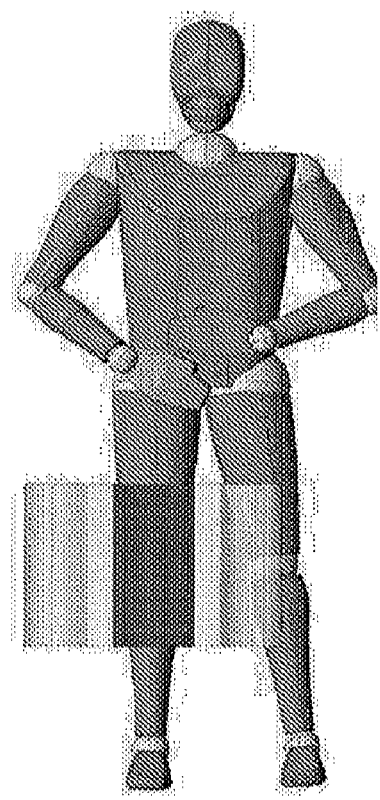
FIGS. 25 and 26 illustrate similar positions of the scanner and of the patient as in FIGS. 23 and 24 while the scanner is the one of FIGS. 15 and 16.
Figure 26:
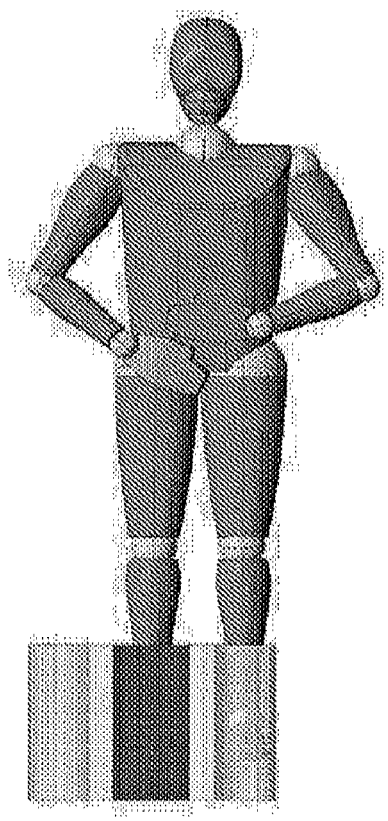

Referring to FIGS. 23, 24, 25 and 26, both scanners according to FIGS. 15 and 17 are oriented with the axis of the chamber C oriented vertically and the patient being in the upright or standing position. FIGS. 23 and 25 illustrate the vertical position of the scanner relatively to the patient leg which is provided for imaging the knee, while FIGS. 24 and 26 illustrates the vertical position of the scanner relatively to the patient leg which is provided for imaging the foot. In this configuration the MRI apparatus according to the present invention allows to carry out imaging in a naturally stressed condition of the legs.

FIG. 29 illustrates a combination of the scanner 1 according to a preferred embodiment of the present invention and particularly according to FIG. 1 with means for blocking the lower limb in a position in which the leg is at the knee. Here the device 40 is formed by a rigid shell having two segments 140 and 240 being oriented according to different directions, i.e. at an angle one with the other. It has to be stressed that the device is illustrated in a very schematic form. In a preferred embodiment the rigid shell has an anatomical shape corresponding to the shape of the part of the limb to which it has to be secured. The shell is secured to the leg by tightening means such as the belts 240 having tightening joints 340 illustrated schematically since known in the state of the art. The shell is destined to be placed against the rear side of the leg and the different orientation of the two shell segments 140, 240, will block the leg when tightened to it in a posture in which the knee is bent. Particularly the bending of the knee might be of 5 to 20°.

There are different ways of configuring the rigid shell and the tightening means. Particularly also the rigid shell can be concave.

Figure 30:
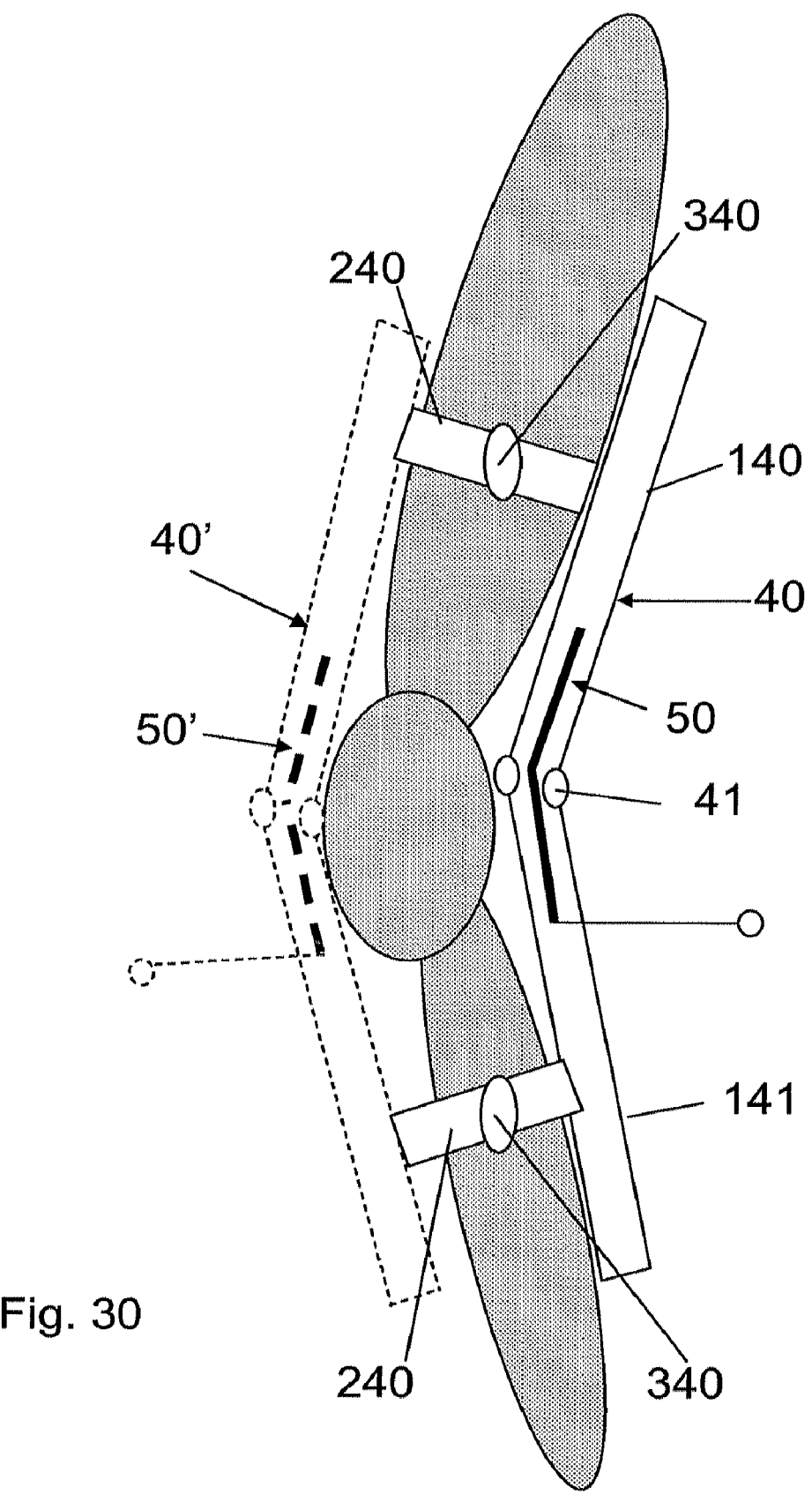
FIG. 30 illustrates schematically a variant of the device for blocking the leg in a predetermined posture in which the MRI signal receiving means are integrated.

As illustrated in FIG. 30, two shells may be provided each one shaped correspondingly to the anatomy of the limb, in particular of the leg, on one of two diametrically opposite sides, such as the front and rear side. The two shells 40, 40' are secured to the limb by means of tightening means 340.

The rigid shell or shells may be also formed by two segments or branches or by more than two segments or branches which are hinged one to the other in such a way as to assume different orientations, means being also provided which allow locking the said segments or branches in a certain relative orientation such as to modify the angle of bending of the leg or arm respectively at the knee and at the elbow.

According to a further improvement the said means for locking the limb in a predetermined position or posture may form the enclosure, the housing or the supporting structure of the receiving means of the MRI signals such as the receiving coils. In FIG. 30 this means are at the level of the knee and are formed by the receiving coil 50 and/or 50' if a further shell 40' is provided.

Figure 31:
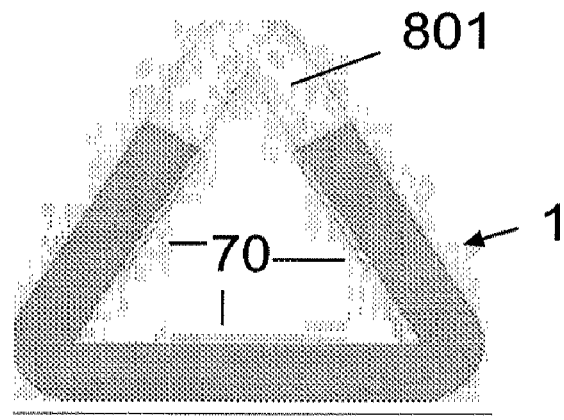
FIGS. 31 to 33 illustrate three different variants of scanners or magnetic structures having an annular cross section open or closed and which have a polygonal cross section respectively triangular. Square or octagonal and which carry respectively three and four magnetic poles.
Figure 32:
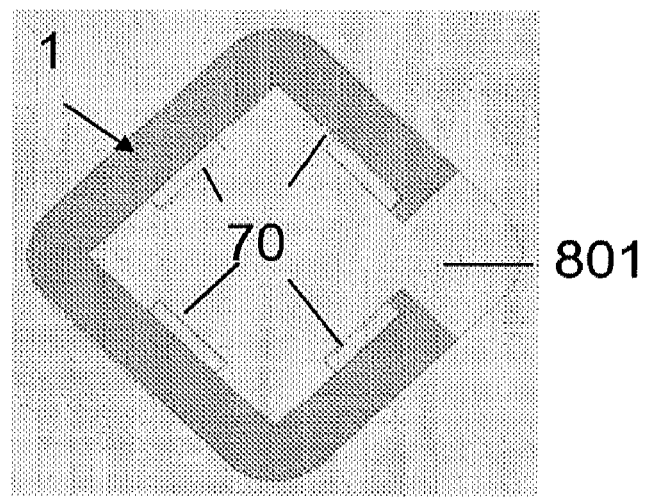
Figure 33:
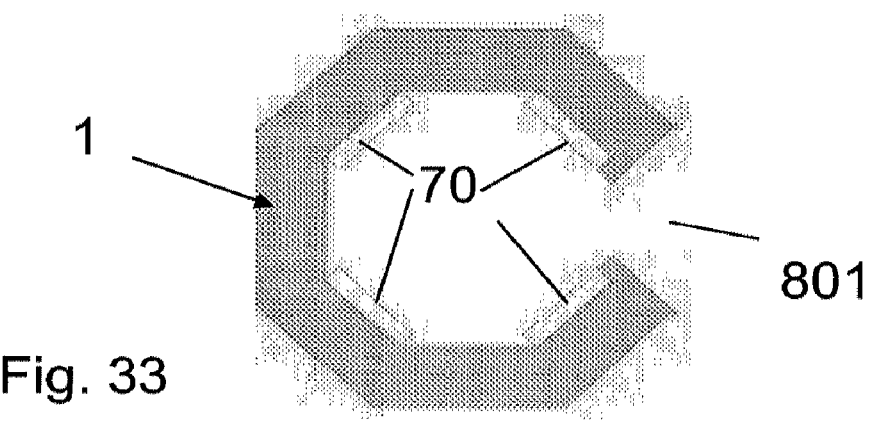

Many different shapes of the scanner and of the chamber cross section may be chosen for the scanner and/or for the chamber C. the examples of FIGS. 31 to 32 illustrates a scanner having a triangular an square and an octagonal cross section or shape and delimiting a chamber or cavity C with the corresponding cross section. Furthermore the lateral opening 801 is provided for the triangular and square scanner at a corner. The triangular scanner has three magnetic poles 70, while the square or octagonal scanner have four magnetic poles. In the square and octagonal scanner the poles 70 are placed on diametrically opposed sides perpendicular to two crossed diameters of the scanner cross section.

Referring again to FIG. 17, the scanner illustrated therein has a magnetic yoke 61 which has a cylindrical form having a lateral opening at the opening 801 this yoke carries diametrically opposed magnetic field generation means 60 which are shaped in cross section as annular segments having an axial length corresponding to the axial extension of the chamber and/or of the Yoke.

The invention claimed is:

1. An apparatus for magnetic resonance imaging of patients with limbs, which apparatus comprises:
    a magnetic structure or a scanner having an open or closed annular cross section, and a predetermined extension, in a direction of an axis of said annular cross section, which magnetic structure or scanner includes a body delimiting a cavity or a chamber for housing at least a part of a patient body and having at least two or three open sides, said open sides providing access to the cavity or chamber (C),
    wherein the magnetic structure or the scanner having an open or closed annular cross section is disposed with the axis of said open or closed annular cross section oriented with at least one component in a vertical direction, and further comprising means for displacing in a vertical direction said magnetic structure or scanner or the patient relative to one another.

2. An apparatus according to claim 1, wherein said apparatus carries out imaging of lower and/or upper limbs of a patient in different conditions of natural stress of the upper and/or lower limbs and which apparatus comprises a scanner, the scanner comprising:
    a chamber for housing at least part of an upper or of a lower limb to be examined, the chamber being opened at two opposite ends, which open ends form openings for the limb to enter and/or exit the chamber;
    the chamber being delimited along a lateral wall having an annular cross section which has an extension of 360° or less, particularly between 360° and 270°;
    the lateral wall having a predetermined extension in a direction of a longitudinal axis of the chamber which passes the two opposite open ends;
    the scanner being provided with means for generating a static magnetic field inside said chamber;
    the scanner being provided with means for transmitting signals for exciting magnetic resonance signals to be generated by the limb or part of limb introduced inside said chamber;
    the scanner being provided further with means for receiving or picking up the magnetic resonance signals emitted by the limb or part of the limb housed inside said chamber,
    wherein the scanner is supported in a position in which the longitudinal axis of the chamber has at least one component oriented in a vertical direction and/or one of the open ends of the scanner is oriented upwards, while means are provided for supporting the scanner and/or at least the limb of the patient in a vertically displaceable way relatively to one another.

3. An apparatus as claimed in claim 1, wherein the cavity or the chamber includes an access opening for a part of a human or animal patient body, and the access opening is oriented upwards, whereas the direction of introduction of the limb in said cavity or chamber through said opening has at least one vertical component, so that, with said limb in the chamber or cavity of the magnetic structure or of the scanner, the limb and the patient assume a natural posture.

4. An apparatus as claimed in claim 1, wherein besides being vertically displaceable, the scanner or the magnetic structure is supported in such a way as to be able to rotate around a longitudinal axis of the chamber or of the cavity.

5. An apparatus according to claim 1, wherein said scanner or said magnetic structure are rotatable around the axis of the said closed or opened annular cross section.

6. An apparatus as claimed in claim 1, wherein the magnetic structure or the chamber of the scanner is oriented with its axis tilted 45° with respect to the vertical and/or horizontal directions.

7. An apparatus as claimed in claim 1, wherein the magnetic structure or the scanner is provided at least one of the lateral walls of the magnetic structure or the scanner having a reduced thickness, which is smaller than the natural distance between the lower limbs of the animal or human patient.

8. An apparatus as claimed in claim 1, wherein the magnetic structure is tilted with its axis at an angle of 45° with respect to the vertical or horizontal direction, vertical and horizontal directions of insertion of the patient body part being provided.

9. An apparatus as claimed in claim 1, wherein said apparatus is provided for imaging lower limbs of animals, possibly of large size, in a natural standing position.

10. An apparatus as claimed in claim 1, wherein the magnetic structure or the scanner further comprises means for generating a static magnetic field in the cavity or in the chamber.

11. An apparatus as claimed in claim 10, wherein an axis of oscillation is parallel or perpendicular to the lines of the static magnetic field generated by the magnet structure.

12. An apparatus as claimed in claim 1, wherein the magnetic structure or the scanner has an open 5 annular cross section, e.g. a C- or U-shape.

13. An apparatus as claimed in claim 12, wherein at least one of the two walls that form the two opposite branches of the magnetic structure or of the scanner body having an open annular cross section, has a thickness that is smaller than the lateral distance between the two limbs and the magnetic structure or the scanner is oriented with the axis of the open side of the magnetic structure or scanner which axis is oriented perpendicular or transverse to the lateral axis of alignment of the two adjacent lower limbs.

14. An apparatus as claimed in claim 1, wherein said apparatus comprises an open-ring or U- or C-shaped magnetic structure or scanner, said magnetic structure or said scanner being disposed with the axis of the annular cross section of the magnetic structure of the scanner oriented vertically and with the open side parallel to said vertically oriented axis, whereas the ends of the walls on the vertical opposite sides that delimit the vertical open side are flared or widened in a step-like manner.

15. An apparatus as claimed in claim 14, wherein said apparatus is used for imaging lower limbs, a lower limb of a pair of lower limbs being received in the cavity of the open annular structure, whereas the other limb is located in the widened area at the vertical open side of said magnet structure.

16. An apparatus as claimed in claim 1, wherein a combination of permanent magnets and resistive or superconducting magnets is provided in said magnet structure.

17. An apparatus as claimed in claim 16, wherein the base magnetic structure for the minimum selectable size, is the one in which the magnetic field is only or substantially generated by permanent magnets, whereas as its size increases, an increasing number of resistive or superconducting magnets are turned on, or the field generating currents supplied to such resistive or superconducting magnets are adjusted.

18. An apparatus as claimed in claim 16, further comprising different configurations of additional magnets to be added and removed or turned on and off and the settings of the magnetic field generating currents to be supplied to additional resistive or superconducting magnets stored therein, each being univoquely related to one of multiple predetermined magnetic structure sizes, the resistive or superconductive correction magnets corresponding to a certain selected magnetic structure size being automatically turned on and/or the permanent correction magnets to be added or removed for said certain selected magnetic structure size being signaled and identified by codes.

19. An apparatus according to claim 1, wherein at the outside of the magnetic structure or of the body of the scanner an indentation is provided which has an extension parallel to the extension of the chamber and which bottom wall has a distance from the opposing wall delimiting the chamber which is smaller than the natural distance between the lower limbs of the animal or human patient.

20. An apparatus according to claim 19, wherein the thickness of the opposing wall may be smaller than it would typically be to fit the average distance between the lower limbs of the smallest patient typically designed to be treated by the magnetic resonance imaging apparatus.

21. An apparatus according to claim 19, wherein the magnetic structure or the scanner has one of the said indentation on opposite sides of the chamber, particularly on diametrically opposite sides of the chamber when the scanner body and the chamber has an annular cross section.

22. An apparatus according to claim 19, wherein the scanner body and the chamber have an annular cross section which is open on one side, the chamber has an opening along the lateral wall having a longitudinal extension from one to the other of the said opened opposite ends and two indentations are provided on opposite sides of a central longitudinal plane of the chamber and of the lateral opening.

23. An apparatus as claimed in claim 1, wherein the magnetic structure or of the scanner is extensible in at least one direction perpendicular to the axis of the open or closed annular cross section.

24. An apparatus as claimed in claim 23, wherein the magnetic structure or scanner body with a closed annular or tubular cross section, said magnetic structure or scanner body having means for generating a static magnetic field within the cavity or chamber and being oriented perpendicular to the axis of said annular cross section or at least with one component perpendicular to said axis, and said magnetic structure being adjustable in length radially and parallel or perpendicular to the static magnetic field and/or perpendicular to the axis of the annular cross section.

25. An apparatus as claimed in claim 23, further comprising means are provided for adjusting the strength or further characteristics of the static magnetic field in response to size variations of the magnetic structure or of the scanner.

26. An apparatus as claimed in claim 25, wherein the field generating means are resistive or superconducting magnets, whereas the characteristics of the magnetic field generated thereby are adapted to the selected size of the magnet structure, by adjusting the magnetic field generating current supplied to the resistive or superconducting magnets and/or by turning on one or more different sets of different additional resistive or superconducting correction magnets, which are further turned on or off depending on the selected magnet structure size.

27. An apparatus as claimed in claim 25, wherein the magnetic structure uses permanent magnets as magnetic field generating means, additional magnetized elements being provided, whose magnetization has predetermined magnitude and direction as determined for a predetermined dimensional adjustment of the magnetic structure, which elements are in predetermined positions in the magnetic structure and have predetermined means for removable attachment to the magnetic structure.

28. An apparatus as claimed in claim 27, wherein said additional magnetized elements are provided in the form of multiple arrays of elements, each array being composed of a given number of elements having a predetermined magnetization, in terms of both magnitude and direction of the magnetization vector, and each of which arrays has means for removable attachment to predetermined parts of the magnetic structure and each of which arrays is designed for integration of a magnetic structure having a minimum base configuration to fit a predetermined size of such magnetic structure and particularly a predetermined length in a direction parallel to the magnetic structure having and open annular cross section.

29. An apparatus as claimed in claim 1, wherein the magnetic structure having an open or closed annular cross section has an open or closed inner shell surface with a square or rectangular plan shape, which delimits a rectangular cavity or chamber that is open at the two opposite transverse sides, particularly perpendicular to the axis of the annular cross section.

30. An apparatus as claimed in claim 29, wherein the magnetic structure has an open shape, and one of the four inner shell walls is at least partly or wholly missing, the annular rectangular or square plan shape being open at least at a portion of one of the walls parallel to the axis of the annular shape.

31. An apparatus as claimed in claim 29, wherein the magnetic structure has at least two diametrically opposite walls with respect to the axis of the annular cross section of the magnetic structure, which diametrically opposite walls support or form magnetic field generating means at least over part of their thickness, i.e. of their radial dimension with respect to the axis of the annular shape.

32. An apparatus as claimed in claim 31, wherein said means may be combinations of permanently magnetized material and metal having a predetermined magnetic permeability or resistive or superconducting magnets formed of combinations of coils and cores or combinations of permanently magnetized material and resistive or superconducting magnets.

33. An apparatus as claimed in claim 32, wherein the walls of the magnetic structure parallel to the axis of the annular cross section of the said magnetic structure, which connect the diametrically opposite walls that support or form the magnetic field generating means are relatively thin, i.e. their thickness is smaller than the minimum distance between the lower limbs of the smallest patient body that can be treated by the apparatus.

34. An apparatus as claimed in claim 32, wherein the magnetic structure is tiltable at an angle of 45°, along an axis parallel to one of the two pairs of diametrically opposite walls, i.e. the connection walls between the walls that form or support the magnetic field generating means or the walls that form or support the magnetic field generating means respectively.

35. An apparatus as claimed in claim 1, wherein the apparatus defines an imaging volume having a non spherical shape, more precisely an elliptical shape with the axis of the ellipse parallel to the direction in which the limb is introduced in the cavity, the magnetic field being shimmed, i.e. optimized, in a volume of space delimited by an ideal ellipsoidal surface.

36. An apparatus as claimed in claim 35, further comprising shimming means, i.e. magnetized or magnetizable shimming elements in the form of resistive or superconducting magnets, which may be turned on and supplied with such correction magnetic field generating currents as to change the orientation of the longer axis of the ellipsoid within which the magnetic field is optimized, in response to a predetermined direction of insertion of the body under examination, i.e. a horizontal or vertical direction and/or to change the ellipsoid size.

37. An apparatus as claimed in claim 36, wherein the field generating means are resistive or superconducting magnets, whereas the characteristics of the magnetic field generated thereby are optimized by shimming in a volume contained in an ideal ellipsoid, by adjusting the magnetic field generating current supplied to the resistive or superconducting magnets and/or by turning on one or more different sets of different additional resistive or superconducting correction magnets, which are further turned on or off depending on the ellipsoid selected for magnetic field optimization.

38. An apparatus as claimed in claim 36, wherein the different configurations of additional optimization, i.e. shimming magnets to be added and removed or turned on and off and the settings of the magnetic field generating currents to be supplied to additional resistive or superconducting optimization or shimming magnets stored therein, each being uniquely related to one of multiple predetermined sizes or multiple predetermined orientations of ellipsoidal surfaces for delimiting the volume within which the magnetic field has to be optimized or shimmed, the resistive or superconducting optimization or shimming magnets corresponding to a certain selected size or a certain predetermined orientation of an ellipsoid being automatically turned on and/or the permanent optimization or shimming magnets to be added or removed for said certain selected size and said certain selected orientation of the ellipsoid being signaled and identified by codes.

39. An apparatus as claimed in claim 36, wherein the magnetic structure uses permanent magnets as magnetic field generating means, additional magnetized elements being provided for shimming the field in a predetermined volume delimited by a predetermined ideal ellipsoid, which additional magnetized elements have a magnetization with predetermined magnitude and direction as determined for one of a set of predetermined ideal ellipsoids of different sizes and orientations, and for a predetermined dimensional adjustment of the magnet structure, and which additional magnetized elements are in predetermined positions in the magnet structure and have predetermined means for removable attachment to further parts of the magnet structure.

40. An apparatus as claimed in claim 39, wherein said additional magnetized elements are provided in the form of multiple arrays of elements, each composed of a given number of elements having a predetermined magnetization, in terms of both magnitude and direction of the magnetization vector, and each of which arrays has means for removable attachment to predetermined parts of the magnet structure and each of which arrays is designed for optimization, i.e. shimming of the magnetic field in a predetermined ellipsoid by integration of a magnet structure having a minimum base configuration.

41. An apparatus as claimed in claim 36, wherein a combination of permanent magnets and resistive or superconducting magnets is provided in said magnet structure.

42. An apparatus as claimed in claim 41, wherein the base magnet structure for a predetermined ideal base volume delimiting surface within which the magnetic field has to be optimized, i.e. shimmed, is the one in which the magnetic field is only or substantially generated by permanent magnets, whereas shimming of the magnetic field in an ideal ellipsoidal volume having a predetermined orientation or a predetermined size is performed by turning on several different resistive or superconducting magnets, or by adjusting the field generating currents supplied to such resistive or superconducting magnets.

43. An apparatus according to claim 1, further comprising means for blocking an upper or lower limb to assume a predetermined posture, particularly to assume a certain ending of the articulation of the said limb, namely the knee or the elbow, which means also are able to block the said limb in the said certain posture.

44. An apparatus according to claim 43, wherein the chamber has an elongated cross section along the plane which is transversal to the longitudinal axis of the said chamber, particularly an elliptic, oval or rectangular cross section which can be closed or open such that at least one dimension or radius of the chamber can be limited to a radius which is slightly greater than the maximum radius of a circle enclosing the biggest limb cross section, while in the perpendicular direction the chamber has a radius which is notatably greater than the said maximum radius of a circle enclosing the biggest limb cross section, thus allowing the said inclined or bent posture of the knee or of an elbow.

45. An apparatus according to claim 43, wherein said blocking means includes a device for blocking an upper or lower limb to assume a predetermined posture comprises at least one rigid shell or surface to be secured against a predetermined part of the limb and which is anatomically shaped in a corresponding way to the shape of part of the limb to which it has to be secured in the predetermined posture of the said limb, while the said shell is secured by means for tightening it to the limb, such as one or more belts or tightening straps surrounding the limb.

46. An apparatus according to claim 45, wherein two or more rigid shells are provided in combination which shells are shaped according to the anatomy of different parts of the limb and which can be secured together to the limb by the said tightening means.

47. Apparatus according to claim 45, wherein there are provided at least two shells which are shaped correspondingly to two diametrically opposed sides of the limb while tightening means are provided for tightening the two shells one against the other thus blocking the limb between them in the posture defined by the shape of the said shells.

48. Apparatus according to claim 45, wherein said blocking device is a device for blocking a leg in a certain condition of bending of the knee, particularly corresponding to a slight flexion of the knee of about 5 to 20 degrees.

49. An apparatus according to claim 45, wherein said rigid shell or shells comprises two or more rigid segments which are connected one with the other thanks to hinge means allowing the said segments to be inclined one with respect to the other.

50. An apparatus according to claim 45, wherein said device for blocking the limb in a predetermined posture is combined with the means for receiving or picking up magnetic resonance signals, said means including MRI receiving coils.

51. An apparatus according to claim 50, wherein rigid shell and/or the tightening means forms the enclosure for housing the said receiving means, or said receiving coils.

52. An apparatus as claimed in claim 45, wherein the magnetic structure having a closed annular cross section is oriented with the axis of the said annular cross section tilted 45° with respect to the vertical or horizontal direction and the inner shell surfaces of the said annular cross section of the magnetic structure, which surfaces delimit and form the shell wall that delimits the patient limb receiving cavity or chamber are flared or outwardly inclined at an angle of 45° and are mutually connected by an intersection edge at an intermediate plane of the magnetic structure, which plane is perpendicular to the axis of said annular cross section.

53. An apparatus as claimed in claim 52, wherein said plane is the median plane perpendicular to the axis of the annular cross section of the magnetic structure.

54. An apparatus as claimed in claim 52, wherein the axis of tilt of the magnetic structure is perpendicular to the static magnetic field generated in the cavity or in the chamber of the said magnetic structure and the magnetic field generating means have a cross section, in a plane parallel to the axis of the annular cross section, provided with one or more steps.

55. An apparatus as claimed in claim 54, wherein the magnetic field generating means are permanent magnets, consist of an array of elements, either magnetized or not, such as blocks or plates, which are connected together and to a bearing member of the magnetic structure, and have rectangular and triangular sections so that the envelope surface of the array of blocks or plates on the cavity side is an inclined surface coincident with the inclined surface of the ideal shape of the inner shell surfaces of the magnetic structure, and particularly a 45° inclined surface when the magnetic structure has a 45° tilt.

56. An apparatus as claimed in claim 54, wherein the magnetic field generating means are permanent magnets and consist of an array of elements, either magnetized or not, such as blocks or plates, which are connected together and to a bearing member of the magnetic structure so that the envelope surface of the array of blocks or plates on the cavity side is a stepped surface approximating the inclined surface of the ideal shape of the inner shell surfaces of the magnetic structure, and particularly a 45° inclined surface when the magnetic structure has a 45° tilt.

57. An apparatus as claimed in claim 56, wherein each step is formed of such a combination of magnetized elements that the magnetic field generated in the widened portion of the step has a higher magnetic potential than the next narrower portion of the step, i.e. closer to the median plane perpendicular to the axis of the annular cross section.

58. An apparatus as claimed in claim 56, wherein a neodymium insert is provided for each step, whose magnetization is oriented parallel to the axis of the annular cross section from the outer end side perpendicular to the axis of the annular cross section to the median plane, still perpendicular to the axis of the annular cross section.

* * * * *